US008012950B2

(12) United States Patent
Muir et al.

(10) Patent No.: US 8,012,950 B2
(45) Date of Patent: Sep. 6, 2011

(54) METHOD TO DIAGNOSE AND TREAT DEGENERATIVE JOINT DISEASE

(75) Inventors: Peter Muir, Madison, WI (US); Ray Vanderby, Jr., Madison, WI (US); Paolo Pepe Provenzano, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 495 days.

(21) Appl. No.: 10/929,919

(22) Filed: Aug. 30, 2004

(65) Prior Publication Data

US 2005/0074800 A1 Apr. 7, 2005

Related U.S. Application Data

(60) Provisional application No. 60/499,105, filed on Aug. 29, 2003.

(51) Int. Cl.
*A61K 31/519* (2006.01)
*A61K 31/65* (2006.01)
(52) U.S. Cl. ............ 514/152; 514/185; 514/258.1
(58) Field of Classification Search .............. None
See application file for complete search history.

(56) References Cited

U.S. PATENT DOCUMENTS

| 6,780,985 | B2 | 8/2004 | Thurmond et al. | |
|---|---|---|---|---|
| 2002/0155166 | A1 | 10/2002 | Choi et al. | |
| 2004/0236074 | A1 | 11/2004 | El-Gewely | |
| 2007/0037835 | A1* | 2/2007 | Ganju et al. | 514/265.1 |
| 2007/0149488 | A1* | 6/2007 | Hlavka et al. | 514/152 |
| 2007/0249708 | A1* | 10/2007 | Holton | 514/449 |
| 2007/0293937 | A1* | 12/2007 | Biggs et al. | 623/1.13 |
| 2010/0137261 | A1* | 6/2010 | Oiva et al. | 514/152 |

FOREIGN PATENT DOCUMENTS

WO   WO 02/32879   *   4/2002

OTHER PUBLICATIONS

CaringMedical.com, Condition: Degenerative Joint Disease, 2009.*
Jauernig et al, Veterinary Surgery, (Mar.-Apr. 2001) vol. 30, No. 2, pp. 132-139.*
Akeson, W.H., Amiel, D., Abel, M.F., Garfin, S.R. and Woo, S.L. (1987). "Effects of immobilization on joints." Clinical Orthopaedics and Related Research (219): 28-37.
Amiel, D., Akeson, W.H., Harwood, F.L. and Frank, C.B. (1983). "Stress deprivation effect on metabolic turnover of the medial collateral ligament collagen. A comparison between nine- and 12-week immobilization." Clinical Orthopaedics and Related Research (172):265-70.
Amiel, D, Frank, C. and Harwood F. et al. (1984). "Tendons and ligaments: a morphological and biochemical comparison." J Orthop Res 1:257-265.
Amiel, D., Ishizue, K.K., Harwood, F.L. et al. (1989). "Injury of the anterior cruciate ligament: the role of collagenase in ligament degeneration." J Orthop Res 7:486-493.

Arcasoy, S.M., Latoche, J.D., Gondor, M., Pitt, B.R., and Pilewski, J.M. (1997). Polycations increase the efficiency of adenovirus-mediated gene transfer to epithelial and endothelial cells in vitro. Gene Ther. 4, 32-38.
Barenberg, S.A., Filisko, F.E. and Geil, P.H. (1978). "Ultrastructural deformation of collagen." Connective Tissue Research 6(1): 25-35.
Bennett, D., Tennant, B., Lewis, D.G., et al. (1988). "A reappraisal of anterior cruciate ligament disease in the dog." J. Small Anim. Pract 29:275-297.
Binkley, J.M. and Peat, M. (1986). "The effects of immobilization on the ultrastructure and mechanical properties of the medial collateral ligament of rats." Clinical Orthopedics and Related Research (203):302-308.
Birk, D.E. and Trelstad, R.L. (1986). "Extracellular compartments in tendon morphogenesis: collagen fibril, bundle, and macroaggregate formation." Journal of Cell Biology 103(1):231-40.
Brandt et al., (1991), Osteoarthritic changes in canine articular cartilage, subchondral bone, and synovium fifty four momths after transaction of the anterior cruciate ligament, *Arthritis Rheum.*, 34;1560-1570.
Bromme, D., Kaleta, J (2002). "Thiol-dependent cathepsins: Pathophysiological implications and recent advances in inhibitor design." Curr Pharm Des 8:1639-1658.
Bromme, D. and Okamoto, K. (1995). "Human cathepsin O2, a novel cysteine protease highly expressed in osteoclastomas and ovary molecular cloning, sequencing and tissue distribution." Biological Chemistry Hoppe-Seyler 376(6): 379-84.
Bune et al., (2001) Mice lacking tartrate-resistant acid phosphatase (Acp5) have disordered macrohage inflammatory responses and reduced clearance of the pathogen *Staphlococcus aureus, Immunology*, 102:103-113.
Comerford et al., (2004), Investigation of the composition, turnover, and thermal properties of ruptured cranial cruciate ligaments of dogs, *Am. J. Vet. Res.* 65:1136-1141.
Daniel, D. M., Stone, M. L., Dobson, B. E., Fithian, D. C., Rossman, D. and Kaufman, K. R. (1994). "Fate of the ACL-injured patient. A prospective outcome study." American Journal of Sports Medicine 22(5):632-44.
de Rooster, H., Cox, E. and van Bree, H. (2000). "Prevalence and relevance of antibodies to type-I and -II collagen in synovial fluid of dogs with cranial cruciate ligament damage." Am J Vet Res 61:1456-1461.
Duval, J.M., Budsberg, S.C., Flo, G.L. and Sammarco, J.L. (1999). "Breed, sex, and body weight as risk factors for rupture of the cranial cruciate ligament in young dogs." J. Am. Vet. Med. Assoc 215:811-814.
Everts, V., Van Der Zee, E. and Creemers, L. et al., (1996). "Phagocytosis and intracellular digestion of collagen, its role in turnover and remodeling." *Histochem J.* 28:229-245.
Everts et al., (2003) Cathespin K deficiency in pycndysostosis results in accumulation of non-difgested phagocytosed collagen in fibroblasts, *Calcif. Tissue Int.*, 73:380-386.

(Continued)

*Primary Examiner* — David A Saunders
(74) *Attorney, Agent, or Firm* — Joseph T. Leone, Esq.; DeWitt Ross & Stevens S.C.

(57) ABSTRACT

Disclosed are methods for detecting and treating joint disease. The methods of diagnosis include determining increased expression of enzymes that are upregulated during the progress of joint and ligament inflammation and degeneration. In addition, disclosed are methods of treating the disease including inhibiting the activity of responsible proteases.

3 Claims, 15 Drawing Sheets

OTHER PUBLICATIONS

Fruensgaard et al., (1989), Incomplete ruptures of the anterior cruciate ligament, *Journal of Bone and Joint Surgery*, British vol. 71(3):526-30.

Galloway et al., (1995), Histopathological evaluation of canine stifle joint synovial membrane collected at the time or repair of cranial cruciate ligament rupture, *J. Am. Anim. Hosp. Assoc.* 31:289-294.

Garnero, P., Borel, O., Byrjalsen, I. and Ferreras, M., et al. (1998). "The collagenolytic activity of cathepsin K is unique among mammalian proteinases." J Biol Chem 273(48): 32347-52.

Garnero et al., (2003) The type I collagen fragments ICTP and CTX reveal distinct enzymatic pathways of bone collagen degradation, *Journal of Bone and Mineral Research*, 18, 859-867.

Gelb, B.D., Shi, G.P., Chapman, H.A. and Desnick, R.J. (1996). "Pycnodysostosis, a lysosomal disease caused by cathepsin K deficiency." Science 273(5279): 1236-8.

Goldberg, V.M., Burstein, A. and Dawson, M. (1982). "The influence of an experimental immune synovitis on the failure mode and strength of the rabbit anterior cruciate ligament." J Bone and Joint Surg 64A:900-906.

Golub, L.M, Lee, H-M and Ryan, M.E. (1998). "Tetracyclines inhibit connective tissue breakdown by multiple non-antimicrobial mechanisms." Adv Dent Res 12:12-26.

Gomori et al., (1952), Microscopic Histochemistry: Principles and Practice, Chicago, University of Chicago Press, 137-221.

Greenwald et al., (1998), In vitro sensitivity of the three mammalian collagenases to tetracycline inhibition: Relationship to bone and cartilage degradation, Bone 22:33-38.

Griffin, D.W. and Vasseur, P.B. (1992). "Synovial fluid analysis in dogs with cranial cruciate ligament rupture." J Am Anim Hosp Assoc 28:277-281.

Hayashi et al., (2003), Histologic changes in ruptured canine cranial cruciate ligament, *Vet. Surg.*, 32:269-277.

Hayman, A.R., Jones, S.J. and Boyde, A. et al. (1996). "Mice lacking tartrate-resistant acid phosphatase (Acp 5) have disrupted endochondral ossification and mild osteopetrosis." Development 122:3151-3162.

Heffron, L.E. and Campbell, J.R. (1978). "Morphology, histology and functional anatomy of the canine cranial cruciate ligament." Vet Rec 102:280-283.

Hewicker-Trautwein, M., Carter, S.D., Bennett, D. and Kelly, D.F. (1999). "Immunocytochemical demonstration of lymphocyte subsets and MHC class II antigen expression in synovial membranes from dogs with rheumatoid arthritis and degenerative joint disease." Vet Immunol Immunopathol 67:341-357.

Hillam et al., (1995), Inhibition of bone resorption and stimulation of formation by mechanical loading of the modeling rat ulna in vivo, *J. Bone Miner. Res.*, 10:638-689.

Honey et al., (2003) Lysosomal cystein proteases regulated antigen presentation, *Nature Reviews*, 3:472-482.

Hou, W. S., Li, Z., Gordon, R. E. and Chan, K. et al. (2001). "Cathepsin K is a critical protease in synovial fibroblast-mediated collagen degradation." Am J Pathol 159(6): 2167-77.

Innes, J.F., Bacon, D., Lynch, C. and Pollard, A. (2000). "Long-term outcome of surgery for dogs with cranial cruciate ligament deficiency," Vet. Rec. 147:325-328.

Janckila et al., (2002) Serum tartrate-resistant acid phosphatase isoforms in rheumatoid arthritis, *Clin. Chim. Acta.*, 320:49-58.

Janckila et al., (2003), Disease specific expression of tartrate-resistant acid phosphatase isoforms, *J. Bone Miner. Res.*, 18:1916-1919.

Kafienah, W., Bromme, D., Buttle, D. J., Croucher, L. J. and Hollander, A. P. (1998). "Human cathepsin K cleaves native type I and II collagens at the N-terminal end of the triple helix." Biochem J 331(Pt 3):727-32.

Lawrence, D., Bao, S., and Canfield, P.J. et al. (1998). "Elevation of immunoglobulin deposition in the synovial membrane of dogs with cranial cruciate ligament rupture." Vet Immunol Immunopathol 65:89-96.

Li, Z., Hou, W.S., Escalante-Torres, C.R., Gelb, B.D. and Bromme, D. (2002). "Collagenase activity of cathepsin K depends on complex formation with chondroitin sulfate." J Biol Chem 277:28669-28676.

Lipowitz et al., (1985), Synovial membrane changes after experimental transaction of the cranial cruciate ligament in dogs, *Am. J. Vet. Res.*, 46:1166-1170.

Lo et al., (2003) Messenger ribonucleic acid levels in disrupted human anterior cruciate ligaments, *Clinical Orthopaedics and Related Research* 407, 249-258.

Muir et al., (2002), Evaluation of tartrate-resistant acid phosphatase and cathepsin K in ruptured canine cranial cruciate ligament in dogs, *Am. J. Vet. Res.*, 63:1279-1284.

Murray et al., (2000), Histological changes in the human anterior cruciate ligament after rupture, *J. Bone Joint Surg.*, 82A:1387-1397.

Nakagawa et al., (1999), Impaired invariant chain degradation and antigen presentation and diminished collagen-induce arthritis in cathepsin S null mice, *Immunity*, 10:207-217.

Narama et al., (1996), Morphogenesis of degenerative change predisposing dogs to rupture of the cranial cruciate ligament, *J. Vet. Med. Sci.*, 58:1091-1097.

Niebauer, G.W., Wolf, B., Bashey, R.I. and Newton, C.D. (1987). "Antibodies to canine collagen types I and II in dogs with spontaneous cruciate ligament rupture and osteoarthritis." Arthritis Rheum 1987;30:319-327.

Oddie GW, Schenk, G. and Angel, N.Z. et al. (2000). "Structure, function, and regulation of tartrate-resistant acid phosphatase." Bone 27:575-584.

Parak, W.J., Dannohl, S., George, M. and Schuler, M.K. et al. (2000). "Metabolic activation stimulates acid production in synovial fibroblasts." Journal of Rheumatology 27(10): 2312-22.

Petersen, W. and Tillmann, B. (1999). "Structure and vascularization of the cruciate ligaments of the human knee." Anat. Embryol 200:325-334.

Provenzano, P.P., Hurschler, C. and Vanderby, R.J. (2001). "Microstructural morphology in the transition region between scar and intact residual segments of a healing rat medial collateral ligament." Connect. Tiss. Res. 42(2): 123-133.

Reddy et al., (1995) Pericellular mobilization of the tissue-destructive cysteine proteinases, cathepsins B, L, and S by human monocyte-derived macrophages, *Proc. Natl. Acad. Sci*, 92:3849-3853.

Reno, C., Marchuk, L., Sciore, P., Frank, C. B. and Hart, D. A. (1997). "Rapid isolation of total RNA from small samples of hypocellular, dense connective tissues." Biotechniques 22(6): 1082-6.

Saftig, P., Hunziker, E., Wehmeyer, O. and Jones, S. et al. (1998). "Impaired osteoclastic bone resorption leads to osteopetrosis in cathepsin-K-deficient mice." Proc Natl Acad Sci U S A 95(23): 13453-8.

Scavelli, T.D., Schrader, S.C. and Matthiesen, D.T. et al. (1990). "Partial rupture of the cranial cruciate ligament of the stifle in dogs: 25 cases (1982-1988)." J Am Vet Med Assoc 196:1135-1138.

Spindler et al., (1996), Expression of collagen and matrix metalloproteinases in ruptured human anterior cruciate ligament: an in situ hybridization study, *J. Orthrop Res.*, 14:857-861.

Stefanini et al., (1967), Fixation of ejaculated spermatozoa for electron microscopy, *Nature*, 216:173-174.

Thielke, R.J., Cooke, M.E., Graf, B.K., Vailas, A.C. and Vanderby Jr., R. (1994). "Intermittent cyclic loading of canine anterior cruciate ligament explants—a tissue culture study." Advances in Bioengineering BED-28: 61-62.

Vanderby, R., Jr., Vailas, A. C. and Graf, B. K. et al. (1990). "Acute modification of biomechanical properties of the bone-ligament insertion to rat limb unweighting." FASEB Journal 4(8): 2499-505.

Van de Wijngaert, F.P. and Burger, E.H. (1986). "Demonstration of tartrate-resistant acid phosphatase in un-decalcified, glycomethacrylate-embedded mouse bone: a possible marker for (pre) osteoclast identification." J. Histochem Cytochem., 34:1317-1323.

Vasseur, P.B. and Berry, C.R. (1992). "Progression of stifle osteoarthrosis following reconstruction of the cranial cruciate ligament in 21 dogs." J. Am. Anim. Hosp. Assoc., 28:129-136.

Vasseur, P.B, Pool, R.R., Arnozky, S.P. and Lau, R.E. (1985). "Correlative biomechanical and histologic study of the cranial cruciate ligament in dogs." Am J Vet Res.,46:1842-1854.

Volk et al., (2003) Gelatinase activity in synovial fluid and synovium obtained from healthy and osteoarthritic joints of dogs, *American Journal of Veterinary Research*, 64, 1225-1233.

Votta, B.J., Levy, M.A. and Badger, A. et al. (1997). "Peptide aldehyde inhibitors of cathepsin K inhibit bone resorption in vitro and in vivo." J. Bone Miner Res12:1396-1406.

Woo, S.L., Gomez, M.A. and Sites, T.J. et al. (1987). "The biomechanical and morphological changes in the medial collateral ligament of the rabbit after immobilization and remobilization." J Bone Joint Surg Am 69(8): 1200-11.

Yu, L.P. Jr, Smith, G.N. and Brandt, K.D., et al. (1992). "Reduction in the severity of canine osteoarthritis by prophylactic treatment with oral doxycycline." Arthritis Rheum 35:1150-1159.

Aspden R.M. Osteoarthrits: a problem of growth not decay? Rheumatology 2008;47:1452-1460.

Chaudhari A.M.W. et al. Knee kinematics, cartilage morphology, and osteoarthritis after ACL injury. Med. Sci. Sports Exerc. 2008; 40:215-222.

Fleming B.C. et al. Ligament injury, reconstruction, and osteoarthritis. Curr Opin Orthop. 2005;16:354-362.

Griffin T.M. et al. Why is obesity associated with osteoarthritis? Insights from mouse models of obesity. Biorheology 2008;45:387-398.

Hanna F.S. et al. Women have increased rates of cartilage loss and progression of cartilage defects at the knee than men: a gender study of adults without clinical signs of knee osteoarthritis. Menopause 2009;16:666-670.

Sakkas L.I. et al. The role of T cells in the pathogenesis of osteoarthritis. Arthritis Rheum 2007;56:409-424.

Hummel, K.M., et al., "Cystein proteinase cathepsin K mRNA is expressed in synovium of patients with rheumatoid arthritis and is detected at sites of synovial bone destruction," J Rheumatol, Oct. 1998, pp. 1887-1894, 10, PubMed.

Bonvoisin et al., 1984, "Increased DNA and/or RNA content of synovial fluid cells in rheumatoid arthritis: a flow-cytometry study," *Ann. Rheumatuc Dis.*, 43:222-227.

Boyle et al., 2003, "Quantitative biomarker analysis of synovial gene expression by real-time PCR," *Arthritis Research & Therapy*, 5:R352-R360.

Deng et al., 2001, "Synovial cytokine mRNA expression during arthritis triggered by CpG motifs of bacterial DNA," *Arthritis Res.*, 3:48-53.

Lemburg et al., 2004, "Immunohistochemical characterization of inflammatory cell populations and adhesion molecule expression in synovial membranes from dogs with spontaneous cranial cruciate ligament rupture," *Vet. Immunol, Immunopathol.*, 97:231-240.

Muir et al., 2006, "Collagen fragmentation in ruptured canine cranial cruciate ligament explants," *The Veterinary Journal*, 172:121-128.

Muir et al., 2007, "OL-3 inhibition of collagen fragmentation in ruptured cranial cruciate ligament explants from dogs with stifle . . . ", *The Veterinary Journal*, 174:403-406.

Rosengren et al., 2003, "Measurement of inflammatory Biomarkers in Synovial Tissue Extracts by Enzyme-Linked Immunosorbent Assay," *Clinical and Diagnostic Laboratory Immunology*, 1002-1010.

* cited by examiner

METHOD TO DIAGNOSE AND TREAT DEGENERATIVE JOINT DISEASE

CROSS-REFERENCE TO RELATED APPLICATION

This application claims priority under 35 USC §119(e) to U.S. Provisional Application Ser. No. 60/499,105, filed 29 Aug. 2003, the entirety of which is incorporated herein.

FEDERAL FUNDING

This work was supported in part by grant NAG9-1152 from the National Aeronautic and Space Administration. The United States Government has certain rights to this invention.

REFERENCES AND INCORPORATION BY REFERENCE

Complete bibliographic citations for the references cited herein are contained in a section titled "REFERENCES," immediately preceding the claims. All of the documents listed in the "REFERENCES" section are incorporated herein.

FIELD OF THE INVENTION

The invention is directed to a method of assaying for preclinical joint disease and a method of treating joint degeneration in both naturally occurring and acute trauma presentations.

BACKGROUND OF THE INVENTION

Joint disease is a common degenerative malady with a huge economic cost as well as a significant loss in quality of life for its sufferers. Joint disease manifests itself in many forms including arthritis, osteoarthritis and rheumatoid arthritis. These disorders have many pathologic events in common and they all result in pain, inflammation, and instability of the joint. In many cases, these disorders can lead to progressive degeneration of the joint with increasing discomfort and difficulty of use.

While any joint can be affected by joint disease, the most common types of joints affected are synovial joints. Synovial joints are marked by the articulation of separate bones that are held together by a fibrous cuff. In addition, the joint capsule is lined by a synovial membrane with the articulating surfaces of the bones covered by cartilage and the joint space filled with synovial fluid. Most joints of the body are synovial joints with the exceptions being fibrous joints, exemplified by the suture joints of the skull, and the cartilaginous joints, exemplified by the symphysis joint of the pelvis.

Though having a wide variation in form, all synovial joints have important structural features in common. These features include: the muscles, which are connected to the bones by tendons; the bursa, which allows the muscle to move smoothly over the joint; the ligaments, which connect the bones to each other and provide a framework to maintain the integrity of the joint; the synovial fluid, which lubricates the joint; the synovial membrane, or synovium, which encloses the interior space of the joint and produces the synovial fluid; and the capsule, which encloses the joint.

The effects of joint diseases such as arthritis, osteoarthritis and rheumatoid arthritis are quite profound. These effects include space loss, eburnation, cyst formation, osteophytosis, malalignment, fibrous ankylosis and in the spine, spondylosis. In addition, arthritis, osteoarthritis and rheumatoid arthritis are all marked by pain and swelling of the joint and are often accompanied by morning stiffness. Inflammatory osteoarthritis is also associated with joint inflammation and can lead to further pathological effects.

While the specific causes of joint diseases are as yet unidentified, the epidemiology is being pieced together. For instance, rheumatoid arthritis is thought to result from persistent inflammation of the joint. The inflammation may be the result of infection or injury. However, in rheumatoid arthritis, the inflammation continues after the infection has subsided or the acute injury has healed. Rheumatoid arthritis is marked by an infiltration of the joint by cells of the immune system, which causes a reaction called synovitis, and results in inflammation of the joint. Synovitis is followed by an abnormal growth of the synovial cells and a thickening of the synovium, which results in further swelling and increased pain in the joint.

Osteoarthritis occurs in about 10% of humans and in 50% of those over 60 years of age. Osteoarthritis is marked by a progressive breakdown of the cartilage and an inflammation of the synovium. Osteoarthritis usually affects the weight-bearing joints first and is known to move from joint to joint once the syndrome has been established. In addition osteoarthritis is also marked by inflammation and synovitis.

Treatments for joint diseases are generally limited to palliative treatments, which ease the pain and decrease the swelling, or invasive surgery to replace the joint. However, a cure or means of limiting the disease has yet to be identified.

Degenerative ligament disease is a form of joint disease, which is a common pathology of larger vertebrates. The most common manifestation of ligament disease in humans is disuse degeneration, partial and complete ligament rupture, and degeneration occurring after traumatic injury to the knee joint. Knee injuries are very common among active individuals. They are the most common injury in skiing and a prevalent injury in a host of other activities, including football, basketball, volleyball, soccer, tennis, and any other sport which requires rapid side-to-side movement. In addition to human joint injuries, joint injuries are common in a number of domestic animals. For instance lameness of the stifle, or rear knee joint in quadrupeds, is a common pathology of dogs, horses and other domestic animals. Stifle joint surgery is the most common elective surgery for dogs. While the knee is the most obvious joint displaying degenerative ligament disease, the disease is not limited to that joint. Other examples of joints that are disabled due to degenerative ligament disease are the acromioclavicular joint near the shoulder, the vertebral column, the hip, the foot and ankle, the hand, the tibiofibular at the lateral aspect of the knee, and the radioulnar joint at the elbow.

The knee joint is comprised of the femur, tibia and the patella. Holding these bones together is the work of important supporting tissues. These tissues are the anterior cruciate ligaments (ACL) and posterior cruciate ligaments (PCL) in humans, and the cranial and caudal cruciate ligaments (CCL) in dogs. In addition, there are other supporting tissues in the joint. These include collateral ligaments, meniscal ligaments, medial collateral ligament (MCL) and the patella tendon. Because of its position as the body's major load-bearing joint, the knee joint receives tremendous stress every day with little opportunity for normal rest. Consequently, this may be one of the reasons that the knee is so susceptible to ligament disease.

In many cases, individuals do not know they have ligament damage until they begin to feel instability in the knee. Frequently, this instability is also accompanied by partial or total rupture of the anterior or posterior cruciate ligaments. After instability has ensued, there are only two treatments: surgery and incapacitation. Both surgery and incapacitation have the same effect; loss of mobility and disuse of the knee joint. Unfortunately, joint disuse is implicated in further joint degeneration.

Ligaments, like other connective tissue, are thought to follow a process of remodeling. Ligaments are a specialized connective tissue, which guide normal joint motion and limit abnormal joint motion. A decline in the normal mechanical behavior of ligaments can result in increased joint laxity, which in turn is associated with degenerative joint disease and osteoarthritis (Daniel et al., 1994). Ligaments are composed primarily of fibroblasts, collagen fibrils, and an additional interfibrillar matrix. Type I collagen is the most abundant collagen in tendon and ligament extracellular matrices. Type I collagen is present in the form of collagen fibrils, which are long filamentous structures that aggregate to form collagen fibers that in turn combine to form fascicles (Birk and Trelstad, 1986, Kastelic et al., 1978, Provenzano et al., 2001).

Collagen fibers, the primary structural element of ligament, are composed of long collagen fibrils that are primarily aligned along the long axis of the tissue but show substantial overlapping and interweaving (Brodsky et al., 1982, Danylchuk et al., 1978, Provenzano et al., 2001). This microstructural organization of collagen fibrils within and across collagen fibers allows the fiber to provide the tissue's exceptional tensile strength under normal physiologic conditions (Barenberg et al., 1978, Viidik, 1972). During disuse, however, the tensile strength of ligament is greatly reduced (Vailas et al., 1990, Vanderby et al., 1990, Woo et al., 1987). Vanderby et al. and Woo et al. have demonstrated that short periods of joint disuse result in substantial loss of tissue stiffness and reduction of load-bearing capacity. After only seven days of disuse through hindlimb unloading, rat medial collateral ligament (MCL) ultimate stress is decreased by more than 25% (Vanderby et al., 1990), while nine weeks of joint immobilization decreases tissue stiffness and reduces ultimate load in rabbit MCLs to 31% of controls (Woo et al., 1987).

Ligaments and tendons, like other connective tissues, modulate their mechanical properties and biochemical composition in response to loading. Microscopic examination of ligament morphology from tissues unloaded in organ culture or from immobilized joints reveals collagen matrix disorganization and abnormal cellular distribution (Akeson et al., 1984, Thielke et al., 1994). In addition, biochemical analysis of ligaments from immobilized joints reveals a reduction in total collagen, increased collagen turnover, increased collagen synthesis and degradation rate with the degradation rate exceeding the synthesis rate (Akeson et al., 1987, Amiel et al., 1983).

Although it is generally accepted that musculoskeletal tissues are mechanotransductive and able to respond to alterations in their loading environment by adaptation of the load-bearing tissue, little is known about the process of ligament modeling and remodeling. Ligaments are required to adapt precisely to joint growth during development, and to respond to joint stresses after maturity. Ligaments when compared to tendons, have more numerous and larger cells, higher DNA content, a larger amount of reducible collagen cross-links, and more type III collagen (Amiel et al., 1984, Petersen and Tillman, 1999). This suggests that ligaments are more metabolically active and have greater adaptive potential than tendons. Normal noninflammatory adaptive remodeling of ligament collagen is thought to occur by intracellular digestion with lysosomal cathepsins, such as cathepsin B and L, after phagocytosis of extracellular matrix collagen by fibroblasts. In contrast, rapid inflammatory remodeling of collagen appears to be mediated by matrix metalloproteinase enzymes (Everts et al., 1996). However, the loss of collagen mass during remodeling of the CCL after rupture does not appear to be mediated by matrix metalloproteinases (Amiel et al. 1989, Spindler et al., 1996).

Rupture of the cranial cruciate ligament (CCL) is a common and crippling problem in dogs, and causes progressive deterioration in limb function over time (Muir et al., 2002). Progressive osteoarthritis and persistent lameness are commonplace, even with surgical treatment (Innes et al., 2000). Furthermore, partial CCL tears that are treated medically with rest and analgesics often progress to complete tears over time. Complete rupture of the CCL occurs because of progressive structural failure over a period of time in most affected dogs, many of which have bilateral disease (Muir et al., 2002, Bennett et al., 1988). Tissue changes that have been identified during progressive CCL rupture in dogs include loss of ligament fibroblasts, transformation of fusiform ligament fibroblasts to an ovoid or spheroid phenotype, and disruption of the normal hierarchical architecture of Type I collagen within the extracellular matrix, including loss of crimp and disruption of ligament fascicles (Vasseur et al., 1992, Whitehair et al., 1993). Dogs with early cruciate disease usually have a stable stifle joint on physical examination because most of the CCL must be ruptured for joint instability to be detected clinically (Heffron and Campbell, 1978). Although various risk factors for CCL rupture have been identified, including age, body weight, and dog phenotype (Duval et al., 1999, Morris and Lipowitz, 2001, Hayashi et al., 2003, Hayashi et al., 2003, Vasseur et al., 1985), the disease mechanism resulting in CCL rupture in dogs is poorly understood.

The conventional wisdom on the epidemiology of ligament disease in humans is that it is the result of acute trauma. In one such instance the ligaments are injured when the lower leg is rotated rapidly with the joint at 20-50 degrees of flexion. Instances of such stress on the knee occur during skiing, playing basketball, volleyball, or other similar activities. In other cases acute knee injury can result from simply taking a bad step on uneven ground. While acute injury may simply be the result of a single traumatic episode, it may also result from sub-clinical ligament degeneration that puts the joint at risk. Further, even without prior disease, acute injury may result in ligament rupture that is either partial or complete. Even when partial, because the treatment is surgical intervention followed by rest, there is a risk of ligament disuse degeneration. However, joint disuse also presents the prospect of continued degeneration of the joint through unidentified mechanisms.

While several enzymes are thought to be responsible for ligament remodeling in a healthy state, the pathologic mechanism leading to ligament degeneration as exhibited in both dogs and in humans during disuse and recovery from disuse or a traumatic injury has not been elucidated. However, this pathologic progress presents an important pathway for identifying degenerative ligament disease and for prophylactically treating ligament degeneration resulting from either pathological causes or from acute injury.

Therefore, it is desirable to find a method of diagnosing ligament disease and a method of treating ligament disease such that radical intervention such as surgery is not necessary and bed rest or disuse degeneration does not become part of the recovery process.

SUMMARY OF THE INVENTION

A first embodiment of the invention is directed to a method of diagnosing joint disease. The method comprises measuring the concentration or the activity of at least one joint disease-diagnostic enzyme in a tissue, cell, or fluid test sample taken from a joint of a test subject. The concentration of the joint disease-diagnostic enzyme is then compared to the corresponding concentration of the same enzyme found in a normal control sample. An elevated concentration of the enzyme in the test sample as compared to the control sample indicates joint disease in the test subject. In the preferred method, the joint disease diagnosed is degenerative ligament disease or synovitis.

It is also preferred that the concentration or activity of an enzyme selected from the group consisting of cathepsin K, cathepsin S, and tartrate-resistant acid phosphatase (TRAP) is measured.

The sample to be tested can be taken from any of the cells, tissues, or fluids of a joint, the preferred samples being synovial fluid, articular synovial membrane, and articular ligament. Measuring the concentration and/or activity of the enzyme can be accomplished using any means for accomplishing such a measurement, either now known or developed in the futures. Preferred methods include polymerase chain reaction (PCR)-based methods and histological techniques.

A second embodiment of the invention is also directed to a method of diagnosing joint disease. Here, the method comprises contacting a test sample of tissue, cell, or fluid from a joint of a test subject with an antibody specific for an enzyme selected from the group consisting of cathepsin K, cathepsin S, and TRAP. Binding of the antibody to the enzyme is detected. The binding detected is then compared to a corresponding binding detected in a control sample from a normal subject. Increased binding in the test sample as compared to the corresponding binding in the control sample indicates joint disease in the test subject.

A third embodiment of the invention is directed to a method of treating joint disease in a subject in need thereof The method comprises decreasing the concentration or activity of an enzyme selected from the group consisting of cathepsin K, cathepsin S, and TRAP in joint cells, joint tissue, or the extracellular joint fluid in the subject. It is preferred the activity of the cathepsin K, cathepsin S, or TRAP is decreased by administering to the subject an amount of an inhibitor selected from the group consisting of cathepsin K inhibitors, cathepsin S inhibitors, TRAP inhibitors, and combination thereof, wherein the amount is sufficient to decrease the activity of cathepsin K, cathepsin S, or TRAP.

The preferred inhibitors are selected from the group consisting of: tetracyclines, beta-lactams, pharmaceutically suitable salts thereof and combinations thereof, including 4-dedimethylaminosancycline NPI-3469, SB-357114, pharmaceutically acceptable salts thereof, and combinations thereof. Additionally, the concentration or the activity of cathepsin K, cathepsin S, or TRAP is decreased by down regulating the translation of cathepsin K-encoding mRNA, cathepsin S-encoding mRNA, or TRAP-encoding mRNA, respectively; or down regulating the transcription of cathepsin K-encoding DNA, cathepsin S-encoding DNA, or TRAP-encoding DNA, respectively.

A fourth embodiment of the invention is directed to a kit for diagnosing joint disease. The kit comprises, in combination: a first containing having disposed therein oligonucleotide primers dimensioned and configured to specifically amplify MRNA and corresponding cDNA encoding an enzyme selected from the group consisting of cathepsin K, cathepsin S, TRAP, and combinations thereof; and instructions for use. Optionally, the kit may comprise a second container having disposed therein buffer suitable for conducting reverse transcription-polymerase chain reaction (RT-PCR) amplification, and/or a third container having disposed therein reverse transcriptase.

A fifth embodiment of the invention is directed to a kit for diagnosing joint disease. Here, the kit comprises primary antibodies specific to an enzyme selected from the group consisting of cathepsin K, cathepsin S, and TRAP; secondary antibodies that bind to the primary antibodies; reagents dimensioned and configured to detect the secondary antibodies that are bonded to the primary antibodies; and directions for use of the kit.

BRIEF DESCRIPTION OF THE FIGURES

In FIG. 1A, an intact ACL from a 74-year old patient with marked chondroid metaplasia and matrix degeneration is seen. Toward the periphery of the image, note the decreased cellularity within the more normal appearing matrix. In FIG. 1B, a ruptured CCL from a 6-year old dog, demonstrates extensive chondroid metaplasia. Note the large size of the cells, and the cloning phenotype. In FIG. 1C, a ruptured ACL from a 16-year old female patient with a moderate amount of regenerative response is shown. In FIG. 1D, a relatively normal-appearing area of a ruptured ACL from a 32-year old male patient is shown. This area shows normal cellularity and crimp pattern.

FIGS. 2A and 2C were stained histochemically for TRAP and counter-stained with Mayer's hematoxylin (which is seen as red in the original color photos, and as black in the black and white reproductions shown here). FIGS. 2B and 2D were stained immunhistochemically for cathepsin K and counterstained with nuclear fast red (which is seen as tan in the original color photos and as grey in the reproductions shown here. Scale Bar=200 μm. In FIGS. 2A and 2B, a moderate number of TRAP$^+$ and cathepsin K$^+$ cells can be seen in a ruptured human ACL. Mild epiligamentous proliferation, a mild regenerative response, and a mild increase in cellularity can also be seen. In contrast, in FIGS. 2C and 2D, obvious epiligamentous proliferation, increased cellularity and regenerative response, and many TRAP$^+$ and cathepsin K$^+$ cells within the core of the ligament can been seen in this ruptured canine CCL.

In FIG. 4A, the black staining for cathepsin K (arrows) can be seen. Nuclear fast red counterstain; bar=50 µm. In FIG. 4B, many cells stained for TRAP also contain black granules of stain, indicating co-localization of cathepsin K (arrows). Bar=50 µm.

FIG. 11A was stained histochemcially for TRAP; FIG. 11B was stained immunohistochemically for cathepsin K, ×200. The joint capsule of the stifle joint is extensively infiltrated with mononuclear leukocytes. FIG. 11A shows TRAP-positive cells that often have a rounded phenotype and are adjacent to the synovial intima or epithelium. FIG. 11B shows cathepsin K-positive cells that are stained black by the DAB reactions and are often found with a rounded phenotype and are also adjacent to the synovial epithelium.

DETAILED DESCRIPTION OF THE INVENTION

Figure 1A:
FIGS. 1A, 1B, 1C, and 1D are photomicrographs of longitudinal frozen sections of human anterior cruciate ligament (FIGS. 1A, 1C, and 1D) and canine cranial cruciate ligament (FIG. 1B) stained histochemically for TRAP, and counter-stained with Mayer hematoxylin. None of the imaged fields contain TRAP$^+$ cells. Scale Bar=100 sum.
Figure 1B:
Figure 1C:
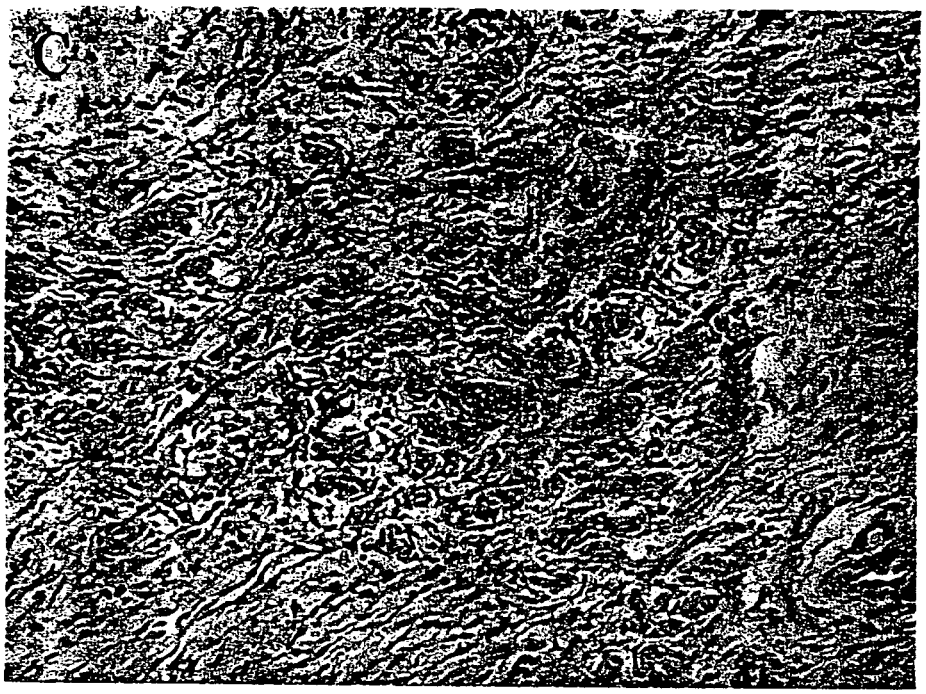
Figure 1D:
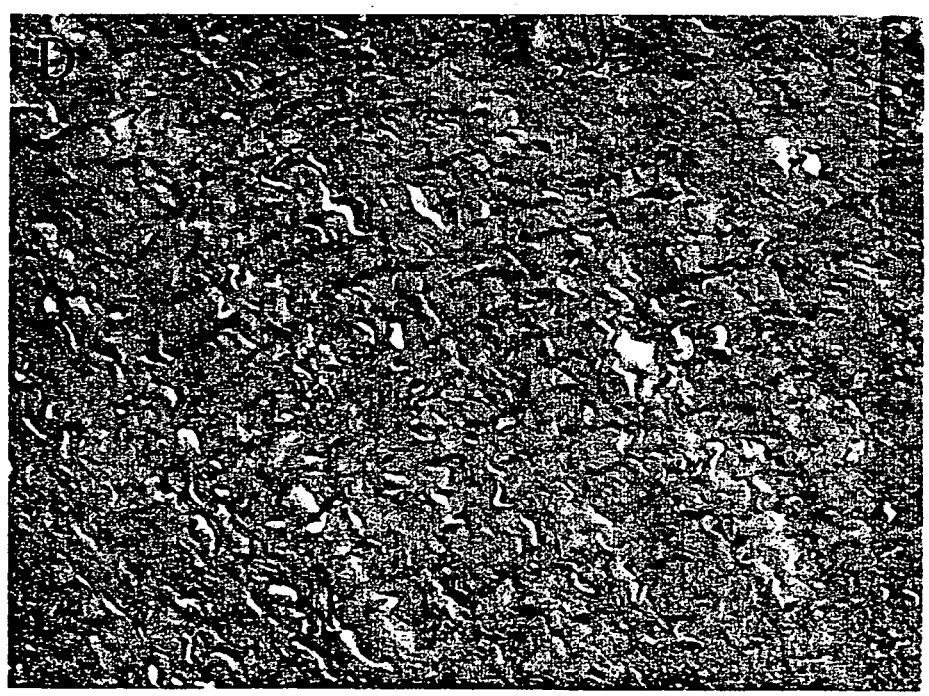

As embodied and broadly described herein, the present invention is directed to a method for identifying and treating degenerative joint disease.

In many cases, joint disease is first noticed when a joint, particularly the knee joint, becomes so unstable that the cruciate ligaments are ruptured or there is a partial tear. Joint instability can arise either through weakening of the ligaments from disuse associated with extreme inactivity, bed rest, joint casting, partial tears, or seemingly spontaneous reasons. Upon surgical intervention the patient must remain non-ambulatory to allow the tissue to recover from the initial and surgical trauma. However, this course of action results in further degeneration of the joint tissues due to disuse. In dogs, cruciate disease is one of the leading causes of stifle lameness. CCL rupture represents 20% of lameness in dogs and is the leading cause for elective surgery in those animals. While similar to degenerative ligament disease in humans, in dogs, stifle lameness is associated with large breeds and old age. Therefore, an investigation into the epidemiology of degenerative ligament disease was pursued using dogs as a model and with young dogs as controls.

In this investigation, dogs exhibiting clinical symptoms of stifle-lameness were identified. Histological analysis of the cranial cruciate ligament in dogs exhibiting stifle-lameness disease revealed that both cathepsin K and TRAP were overexpressed in the fibroblasts of the ruptured ligament as compared to healthy ligament tissue, as well as leukocytes with a rounded phenotype that have migrated into the ligament tissue. See FIGS. 1A-1D, and FIGS. 2A-2D. In addition, in cases where the dog was aged and exhibiting degenerative changes to the ligament matrix in the absence of rupture, histologic analysis showed positive TRAP staining even within the ligament fascicles. In instances of both TRAP and cathepsin K staining, as well as fibroblasts with a fusiform morphology, leukocytes that have infiltrated the ligament and are positively stained exhibit a rounded morphology. In addition, PCR analysis of the synovial fluid of the joint using primers specific for cathepsin K surprisingly resulted in a product for the cathepsin K RT-PCR. This PCR product was not found in healthy dogs. These findings illustrate that cathepsin K may be a causal factor in joint inflammation and ligament degeneration. Moreover, even if cathepsin K up-regulation is only a response to the ligament degeneration, its elevated presence is definitely indicative of ligament degeneration.

Experiments to examine the role of cathepsin K and MMPs were also carried out with particular emphasis to disuse degeneration. In these experiments, the activity of cathepsin K in ligaments from ambulatory and unloaded hindlimbs was examined and compared to levels of the matrix metalloproteinases 2 and 13 (MMP-2, MMP-13) one of the main families of proteases implicated in collagen degradation. To test the role of these enzymes in the degeneration of ligaments, a rat model was used with the animal prepared so as to render the hindlimbs non-ambulatory. In this assay, developed by NASA to test the effects of weightlessness, rats are put in a harness and supported by their tails so that the hindlimbs are supported above the floor of the cage. The rats continue to be ambulatory by use of their front limbs and can, in other respects, carry out their normal behavior.

Figure 6:
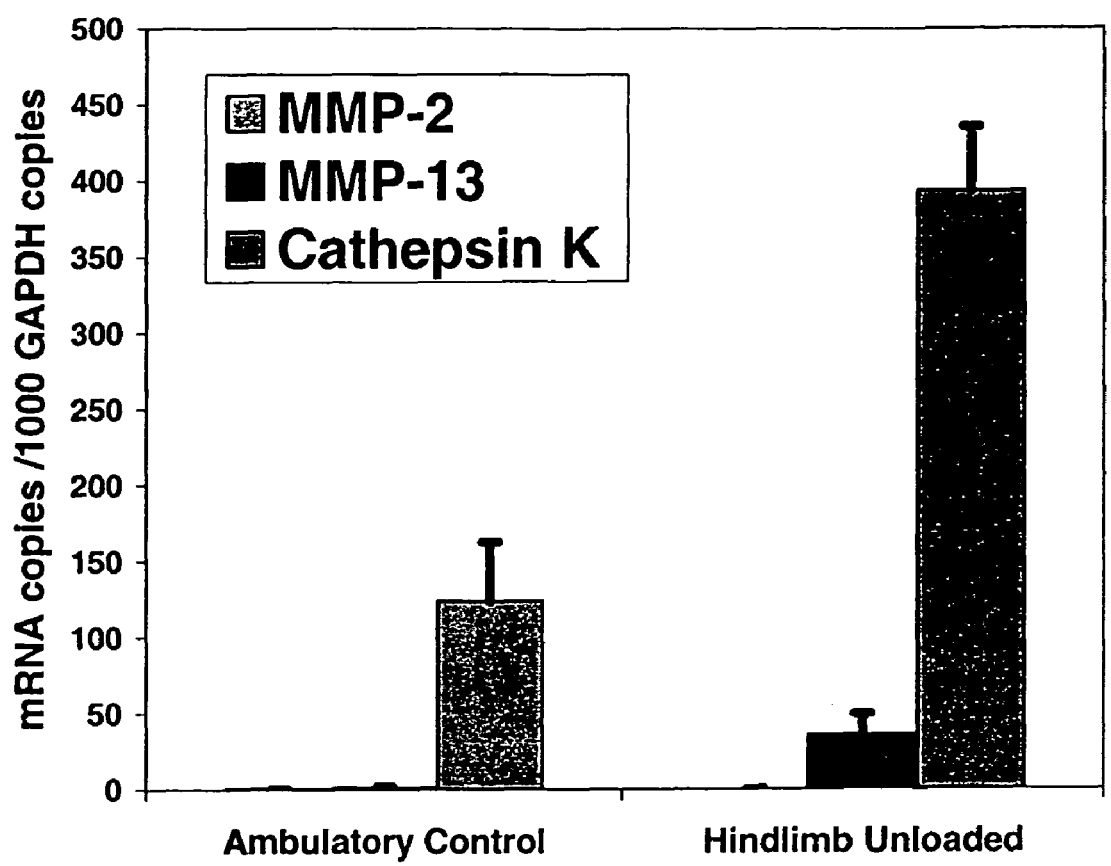
FIG. 6 is a histogram illustrating cathepsin K, MMP-2 and MMP-13 mRNA levels in medial collateral ligaments from ambulatory control and hindlimb-unloaded animals. mRNA levels of the potent protease cathepsin K are substantially increased in tissues subjected to disuse through hindlimb unloading. MMP-13 values are also increased but are not as high as cathepsin K levels. Normalizing by total RNA revealed a nearly identical trend (not shown). Each point represents the mean and standard deviation of triplicate determinations.
Figure 7A:
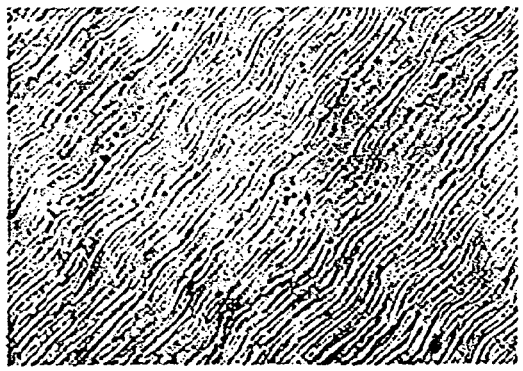
FIGS. 7A, 7B, 7C, 7D, 7E, and 7F are a series of photomicrographs showing the results of immunohistochemical staining for cathepsin K in medial collateral ligaments (MCLs) from ambulatory (FIG. 7A, FIG. 7B, and FIG. 7C) and hindlimb-unloaded rats (FIG. 7D, FIG. 7E, and FIG. 7F) (200×). Each slide was taken from a different animal. In ambulatory tissues cathepsin K (dark spots) was largely localized to spindle-shaped cells between collagen fibers, as is characteristic of fibroblasts. Unloaded tissues had more numerous staining for cathepsin K in spindle- and round-shaped cells than are present in the extracellular matrix, which appears more disorganized. No cell counterstaining was done in these samples.
Figure 7D:
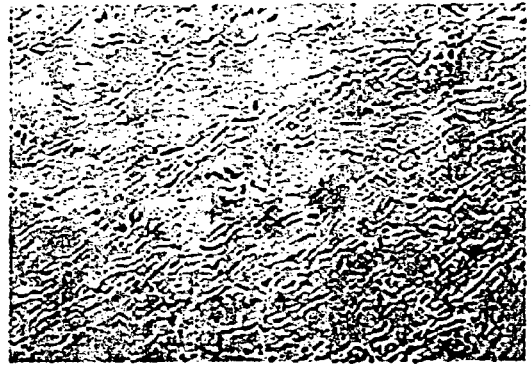
Figure 7B:
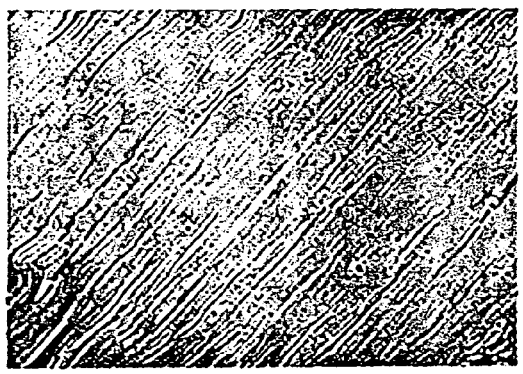
Figure 7E:
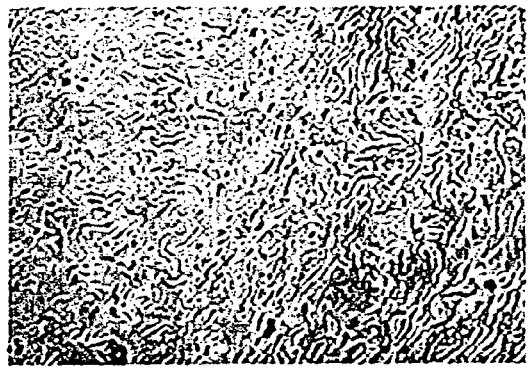
Figure 7C:
Figure 7F:
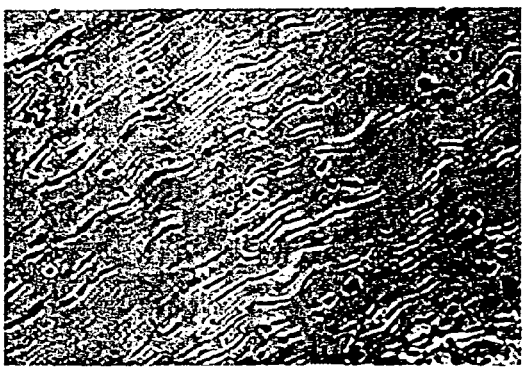
Figure 9:
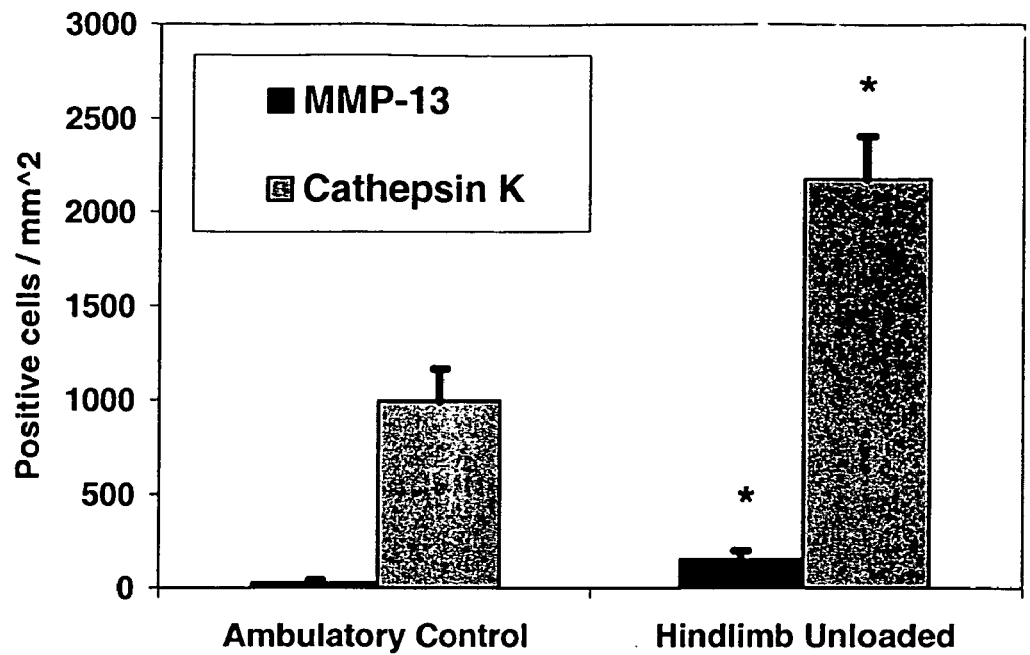
FIG. 9 is a histogram showing the results of cells stained for cathepsin K or MMP-13 in ligaments from ambulatory and hindlimb-unloaded animals (mean±s.d.). The asterisk (*) indicates a statistically significant increase in positively staining cells in tissues from hindlimb-unloaded animals as compared to tissues from ambulatory controls, p=0.002 and 0.047 for cathepsin K and MMP-13, respectively.
Figure 10:
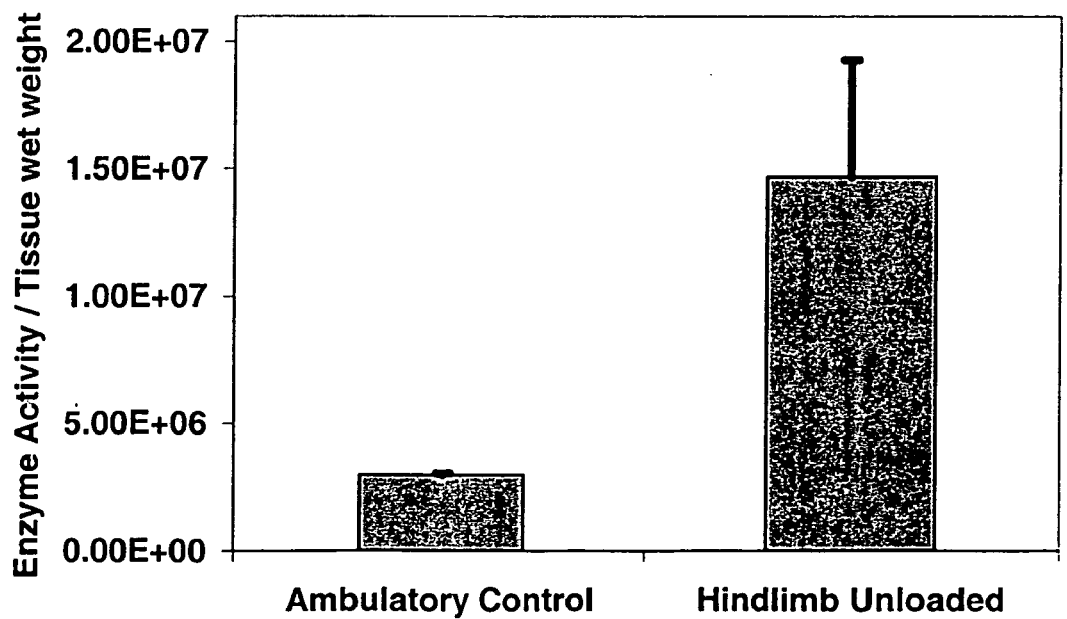
FIG. 10 is a histogram illustrating the results of analysis of cathepsin K enzyme activity in ligaments from ambulatory control and hindlimb-unloaded rats (mean±s.d.). Cathepsin K activity was significantly greater in tissue subjected to disuse (p=0.047).

Results of the rat disuse experiments confirmed substantial differences between ambulatory control and hindlimb-unloaded animals. The results of RT-PCR on mRNA from control and unloaded animals showed an increase in cathepsin K mRNA level on the order of three-fold for the unloaded animals over the controls. The results for MMP-13 concentrations showed an increase of over 30-fold in mRNA levels for the unloaded animals when compared to controls. However, even at this level, increased MMP-expression still resulted in fewer copies of MMP-13 than cathepsin K. A third enzyme, MMP-2, showed no change. These results are shown in FIG. 6. Immunohistochemical staining of the tissues for cathepsin K revealed the characteristic presence of positively stained spindle-shaped cells between the collagen fibers for the control animals (FIGS. 7A, 7B, and 7C); however, the non-ambulatory animals (FIGS. 7D, 7E and 7F) revealed significantly increased staining for cathepsin K both within the spindle cells and in morphologically abnormal rounded cells present in the highly disorganized extracellular matrix. In contrast, immunohisotchemical staining for MMP-13, in control and experimental groups, showed only a minor increase in staining in the experimental group. See FIGS. 8A, 8B and 8C. Quantification of the positively staining cells for both cathepsin K and MMP-13 showed a much greater increase in cathepsin K staining cells than for MMP-13 staining cells. See FIG. 9. These results indicate that the increase in cathepsin K mRNA resulted in a much greater distribution of cathepsin K in the tissues showing abnormal morphology as seen in the non-ambulatory histologic samples than MMP-13. Therefore, an analysis of cathepsin K activity was performed. This data, shown in FIG. 10, illustrates a significant increase in cathepsin K activity in the hindlimb-unloaded animals as compared to the ambulatory controls.

Together, this evidence suggests that cathepsin K is involved in the tissue degeneration exhibited by the non-ambulatory or disuse animals. Further, the evidence suggests that cathepsin K is a viable target for modification and therapeutic approaches to attenuate ligament disuse degeneration.

Following the observation of the inflammation of the CCL and the appearance of morphologically rounded leukocytes shown in FIGS. 2A-2D and 3, an investigation specifically directed to the state of the synovium was made. Sections of synovial membrane from a dog with CCL rupture were made and stained for TRAP (FIG. 11A) and cathepsin K (FIG. 11B). The results indicate that protease positive cells are intimately associated with the inflamed synovial membrane. This suggests that cathepsin K may be related to the inflammatory response that is one of the hallmarks of joint disease.

Subsequent studies comparing gene expression in dogs suffering from CCL damage to both young and old normal dogs suggest that expression of another cathepsin enzyme, cathepsin S, may, in some circumstances, be a more sensitive indicator of CCL damage or disease.

Diagnosing Degenerative Joint Disease

Therefore a first embodiment of the invention comprises a method for diagnosing degenerative ligament disease. In some embodiments, the method comprises detecting an increase in cathepsin K, cathepsin K activity, or cathepsin K gene expression in the affected ligament or the extra-cellular milieu near the affected ligament. In other embodiments, the method comprises detecting expression of the cathepsin S gene. In still other embodiments, the method comprises detecting expression of a TRAP gene. The detection step may comprise histologic analysis performed on samples taken from any suspected joint or ligament. Further, the detection step may comprise a PCR analysis of the sample. In a preferred embodiment, the sample tested is a sample of synovial fluid from the affected joint. In other embodiments, the sample tested is CCL tissue. In this way, positive identification of degenerative ligament disease can be made.

There are many well-known methods for histologic identification of proteins. For example, methods for quantitatively measuring proteins, such as ELISA analyses, are well known. Kits for measuring levels of many proteins using ELISA assays are commercially available from many suppliers. In addition, methods for developing ELISA assays in the laboratory are well known. See for example Antibodies: A Laboratory Manual (Harlow and Lane Eds., Cold Spring Harbor Press). Antibodies for use in such ELISA methods are either commercially available or may be prepared using well-known methods.

Traditionally, protein concentrations are measured by assaying the protein itself However, newer methods amplify the genetic message, mRNA, from which the protein is translated. Therefore, one favored embodiment of the invention is a method to prophylactically assess the incidence of degenerative ligament disease by assaying for the presence of increased expression of cathepsin K, cathepsin S or TRAP in a ligament or joint.

While increased cathepsin K, cathepsin S or TRAP can be determined by various assays, including histological examination and determinations of protease activity, it has been surprisingly found that the synovial fluid of the joint itself can be assayed by RT-PCR for the presence of the cathepsin K, the cathepsin S or TRAP RNA message (mRNA). Without being limited to any mechanism as to how the RNA comes to be present in the synovial fluid, it is possible that the RNA is released from damaged cells. Or, alternatively, leukocytes associated with joint and containing the RNA message are present in the synovium when a sample is taken (The presence of leukocytes in a joint has been previously shown, Galloway and Lester 1995. Nevertheless, by subjecting the synovial fluid to an RT-PCR reaction, the cathepsin K or cathepsin S mRNA can be amplified and identified.

Further, in assaying for cathepsin gene expression using PCR it is possible to utilize different PCR techniques to gather different information. For example, RT-PCR can be employed by the investigator if degenerative ligament disease is suspected in the absence of clinical symptoms.

In the context of clinical diagnosis of degenerative ligament disease, it is desirable to develop a method of accurately measuring cathepsin K, cathepsin S or TRAP levels at very low concentrations with a high level of significance, i.e., a test with a high specificity and a high sensitivity. Thus, a small increase in actual expression over time would have a high level of significance while the actual concentration of cathepsin K (and ligament degeneration) is still quite low. One method to quantify the expression of cathepsin K, cathepsin S or TRAP is quantitative PCR.

The use of mRNA as a means of indirectly measuring protein concentrations has further advantages. First, mRNA, when transcribed, is present in many copies, the number of which is directly correlated to the level of the gene's induction. Second, PCR amplifies the message such that a very low level of the message can be accurately identified. Finally, when the reaction is properly controlled, the level of expression can be statistically quantified (quantitative PCR) such that small increases in protein expression, as measured by mRNA transcription, are significant. Thus, a more sensitive approach to detecting of low levels of circulating cathepsin is detecting mRNA coding for the cathepsin protein rather than detecting the protein itself.

One PCR method to diagnose ligament degeneration is reverse transcriptase PCR (RT-PCR). RT-PCR is a method whereby mRNA is first reverse transcribed resulting in a cDNA copy for every RNA genomic message. This is a powerful tool because mRNA reflects the level of expression of a gene and the reverse transcribed cDNA is devoid of introns found in the genomic copy. Therefore, only the expressed gene is amplified and error represented by mispriming of the genomic copy is easily identified. By reverse transcribing the mRNA, a complementary DNA (cDNA) copy is synthesized. The cDNA is then used in conventional PCR. Due to its sensitivity, RT-PCR is able to amplify RNA messages present at about the zeptomole ($10^{-21}$) level. Kits for performing RT-PCR are commercially available from, for instance, Promega Corporation (Madison, Wis.), which produces the Access RT-PCR™ system and the ImProm-II™ kit, and Ambion Inc, (Austin, Tex.) which markets the RETROscript™ Kit, to name a few.

Further, real-time or quantitative PCR can be utilized so that the progression of the expression of the desired gene can be determined, thereby predicting the severity of the degenerative ligament disease. In quantitative PCR, a double-stranded DNA dye or marker, such as ethidium bromide or Sybr® green, is added to the PCR reaction. Because the marker binds only to double-stranded DNA, as the PCR product increases, the intensity of the marker also increases. Under proper conditions, there is a direct correlation between the amounts of PCR product and detected dye. By determining the increase in cathepsin K or S or TRAP message during a period of observation, the progress of ligament degeneration can be followed over time.

Briefly, for PCR analysis, a sample of the desired tissue or extra-cellular fluid is taken. In some embodiments, the sample is of a ligament suspected of pathological ligament degeneration. In other embodiments, the sample is synovial fluid from the joint cavity. Following well-known methods, the RNA present in the sample is purified and can be used directly in the PCR using specific primers or can first be subjected to reverse transicrptase to provide a cDNA copy. Alternatively, total mRNA can be purified by exploiting the poly-A tail of the mRNA using commercially available kits. For example, QIAGEN produces an mRNA midi kit (Cat. No. 70042) and the Promega Corporation markets PolyATract® mRNA Isolation Systems (Cat. No Z5200), to name a few.

RT-PCR can be carried out using commercially available methods such as the TaqMan® Gold RT-PCR Kit, (Applied BioSystems Foster City, Calif., Cat. No. 4304133) and Absolutely RNA™ RT-PCR Miniprep Kit (Stratagene, La Jolla, Calif., Cat. No. 400800). Total RNA may be reverse transcribed using either specific primers or random hexamers commercially available from, for example, Applied Biosystems (Cat. Nos. N8080128 and N8080127 respectively). The cDNA is amplified using primers specific for the gene of interest.

Figure 12:
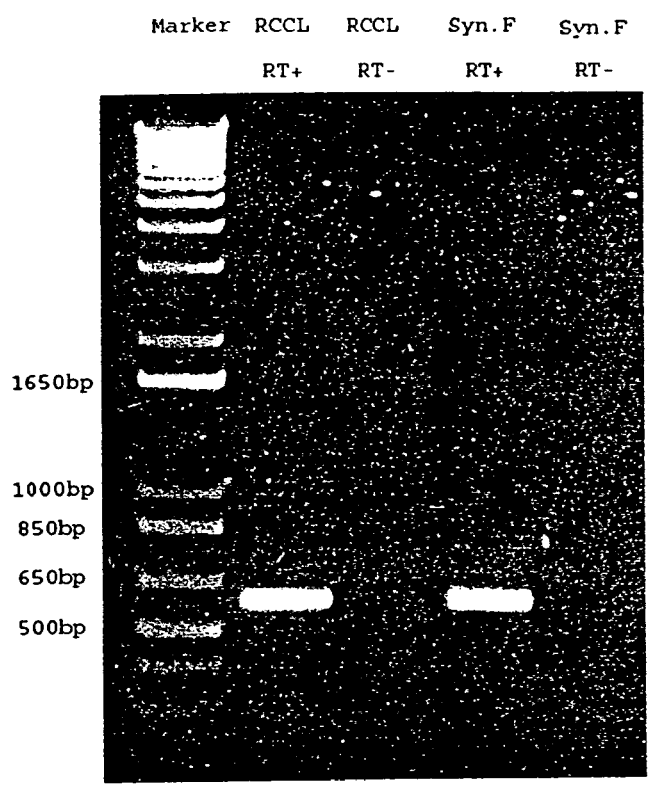
FIG. 12 is a photograph of a 1.2% agarose gel showing the products of an RT-PCR reaction using primers specific for cathepsin K. In this example, mRNA was extracted from canine ruptured CCL (RCCL) and stifle synovial fluid (Syn.F). RT+ indicates lanes with the reverse transcriptase enzyme; RT− indicates control lanes without the reverse transcriptase enzyme. The expected size of the PCR products is 578 bp. PCR was performed for 30 cycles.
Figure 13:
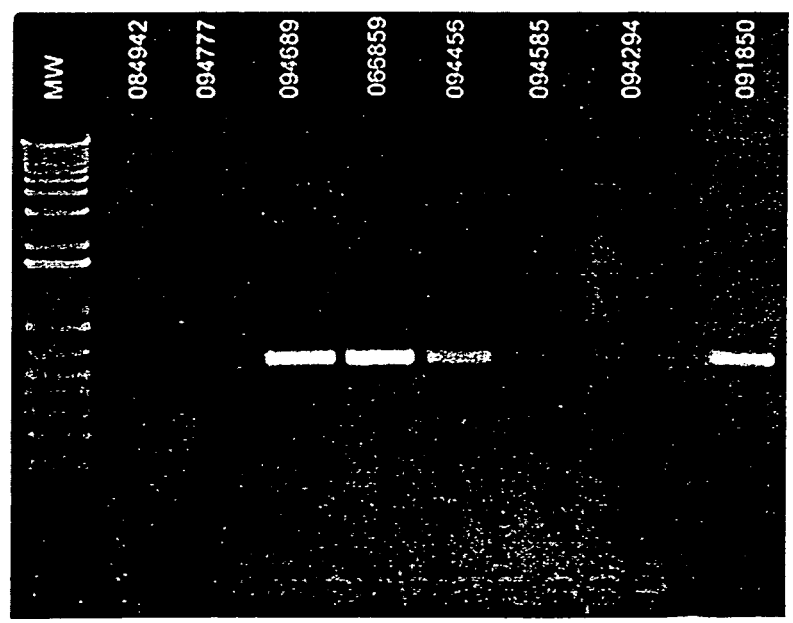
FIG. 13 is a 1.2% agarose gel showing the products of an RT-PCR reaction using primers specific for cathepsin K. In this example, the template mRNA was extracted from synovial fluid from dogs with suspected degenerative ligament disease of the stifle joint. The primers and reaction conditions are the same as for the products illustrated in FIG. 12.

After the cDNA has been synthesized from the mRNA, traditional PCR can be used to amplify specific sequences within the cDNA. By increasing the fidelity of the PCR reaction the sensitivity of the assay increases such that misprimed sequences, pseudogenes and genomic contaminants are not confounding factors for identifying asymptomatic ligament degeneration. Some methods to increase the fidelity of PCR reactions include using a modified Taq polymerase that is heat activated such that primer polymerization does not occur until the PCR reaction is at optimum temperatures. Such polymerases are commercially available from, for example, Applied BioSystems (AmpliTaq Gold, Prod. No. 4311806). By detecting the presence of the upregulated cathepsin K or S or TRAP message, diagnosis of degenerative ligament disease can be made. Further, by using quantitative RT-PCR the change in expression of the cathepsin K or S or TRAP message over time can be followed. For example, RT-PCR reactions can be run on samples of ligaments or synovial fluid taken from sites of suspected ligament degeneration during a first instance of instability or pain. The level of mRNA can be quantitatively determined using RT-PCR. Following treatment with analgesics or anti-inflammatory drugs, the level of mRNA can again be quantitatively measured. A change in expression of cathepsin K or S or TRAP mRNA levels will then be indicative of regression or progression of the disease, even in the absence of symptoms. FIGS. 12 and 13 illustrate the amplification of cathepsin K or S or TRAP mRNA in samples taken from synovial fluid and ruptured cranial cruciate ligament in dogs with degenerate ligament disease (FIG. 12) and dogs suspected of having degenerate ligament disease (FIG. 13).

This valuable information allows a care giver to follow the progress of the disease over time and make more informed treatment decisions, especially with respect to invasive forms of treatment.

Treatment of Degenerative Joint Disease

In another embodiment, the invention is a method of treating degenerative ligament disease by inhibiting cathepsin K or S or TRAP activity. The activity of cathepsin K can be affected at several points of its expression-to-activity cascade, including at the DNA, the RNA, and protein levels.

Methods to Alter Gene Expression:

There are many ways of affecting gene expression and, in the case of cathepsin K, down regulation can be accomplished in several ways. For example, it has been shown that antisense RNA introduced into a cell will bind to a complementary mRNA and thus inhibit the translation of that molecule. In a similar manner, antisense single-stranded cDNA may be introduced into a cell with the same result. Further, co-suppression of genes by homologous transgenes may be effected because the ectopically integrated sequences impair the expression of the endogenous genes (Cogoni et al., 1994) and may also result in the transcription of antisense RNA (Hamada and Spanu, 1998). Methods of using short interfering RNA (siRNA) to specifically inhibit gene expression in eukaryotic cells have also recently been described (Tushchl et al., 2001). In addition, stable triple-helical structures can be formed by bonding of oligodexyribonucleotides (ODNs) to polypurine tracts of double stranded DNA (Rininsland, 1997). Triplex formation inhibits DNA replication by inhibiting transcription of elongation and is a very stable molecule.

Nucleotide sequences such as siRNA and ODNs can be introduced by methods well known in the art. For example, adenovirus vectors having a defective origin of replication can carry a desired transgene. Upon infection, the transgene will be expressed by the vector, but due to the damaged origin, the vector cannot replicate itself, thereby limiting the possibility of sustained wild-type infection. See for example Verma, and Somia, (1997) and Arcasoy et al. (1997).

Methods to Inhibit Protein Activity:

Cathepsin K or S activity can be altered by several methods. In one approach, antibodies specific to cathepsin K may be used to bind the protein, thereby blocking its activity. Such antibodies are commercially available from CHEMICON International, (Temecula, Calif.) and United States Biological (Swampscott, Mass.) to name a few. In addition, other ligands may act similarly to block the ability of proteases to bind to their target and initiate proteolysis. A further means of inhibiting cathepsin K or S or TRAP activity is to interfere with expression of the gene encoding the protein. One such method is via interfering RNA, i.e. RNAi, such as small interfering RNA (siRNA) or short hairpin RNA (shRNA). Methods for designing RNAi molecules and introducing them into cells are described, e.g. in Zheng L et al., *Proc Natl Acad Sci USA*. 2004 Jan 6; 101(1): 135-40.

Pharmacologic methods are also contemplated to affect the activity of cathepsin K or S. Any pharmacologic means which acts to decrease the activity of the indicated proteases is sufficient to carry out the invention. For instance, 4-dedimethylaminosancycline (COL-3, CollaGenex Pharmaceuticals, (Newtown, Pa. USA), NPI-3469 (NAEJA Pharmaceuticals, Edmonton, Alberta, Canada) and SB-357114 (GlaxoSmithKline, King of Prussia, Pa.) are shown to be specific inhibitors of cathepsin K activity.

NPI-3469 is the investigative drug designation for the compound 5-(carbobenzoxy-L-leucyl)amino-2,2-tetramethylene-2,3-dihydro-1H-pyrimidin-4-one:

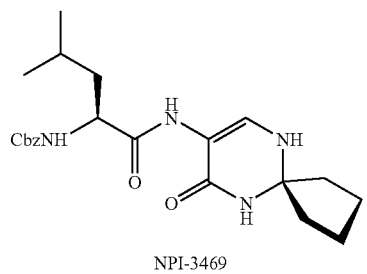

NPI-3469

Regarding SB-357114, see Stoup et al., "Potent and selective inhibition of human cathepsin K leads to inhibition of bone resorption in vivo in a nonhuman primate. *J. Bone Miner. Res*. (October 2001) 16(10):173946 This compound has the following structure:

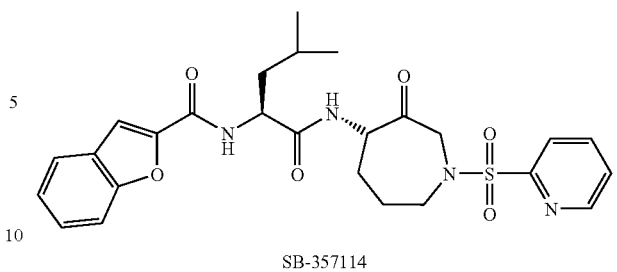

SB-357114

Other classes of drugs shown to be cathepsin K inhibitors include: hydrazide deriviatives, diamino pyrrolidinone aldehydes, acyclic and cyclic ketones and their nitrile derivities, epoxysuccinyl analogues, beta-lactams, vinyl sulphones, chemically modified tetracyclines, heterocyclic amine derivatives, beta ketoethers and their alcohol derivatives, N-cyanomethylamides, epoxysuccinamide derivatives, furanone derivatives, cyanamides and azepanon derivatives (Bromme and Kaleta, 2002, Lecaille et al., 2002). By administering a cathepsin K inhibitor in an effective dose, the pathologic effects of cathepsin K on ligament degeneration and joint disease may be inhibited while the normal housekeeping activity of the protein is left intact for such functions as bone remodeling and non-pathologic ligament remodeling.

The methods of the present invention may be used prophylactically to prevent the development or progression of degenerative ligament disease.

The present invention also provides kits having appropriate primers and reagents for the PCR analysis of synovial fluid for the identification of cathepsin K or cathepsin S or TRAP.

The present invention, thus generally described, will be understood more readily by reference to the following examples, which are provided by way of illustration and are not intended to be limiting of the invention.

EXAMPLE 1

Identification of Cathepsin K in Age-Related Ligament Degeneration

Selection of dogs: Portions of CCL were collected from 30 dogs with CCL disease, which was confirmed at the time of surgical treatment during lateral or medial parapatellar arthrotomy, resection of damaged meniscus, and extracapsular stabilization with nylon suture. Complete CCL rupture was diagnosed if joint instability was detected on physical examination, indicating extensive biomechanical degradation of the CCL. Partial CCL rupture was diagnosed if the affected stifle joint was stable on physical examination. In addition, CCL specimens were collected from 8 aged dogs and 9 young dogs, where aged dogs were 10.0 plus or minus 3.7 years old, and young dogs were 1.7 years old plus or minus 0.9 years without CCL disease that were humanely euthanized by use of IV administration of barbiturates for reasons unrelated to our study. The group of aged dogs was selected to control for the degradation in ligament mechanical properties that is known to occur with aging (Vasseur et al., 1985), and the group of young dogs was selected as one of the controls used to validate our histochemical and immunohistochemical staining. Age, weight, sex, and duration of lameness for each dog were determined.

Specimen collection and preparation: Remnants of ruptured CCL were excised from the femoral and tibial attachment sites in affected dogs. In dogs with normal CCL ligaments, the entire ligament was collected. Immediately after collection, ligament specimens were placed in tissue cassettes and fixed in Zamboni fixative (Stefani et al., 1967) for 1 to 2 days at 4° C. Longitudinal frozen sections, 10 μm thick, were cut and mounted on glass slides for histologic examination. Multiple slides were created from each specimen for histochemical and immunohistochemical staining, in addition to staining with H&E.

Histochemistry: Histochemical staining specific for TRAP was performed on all ligament specimens, and was based on established methods (Van de Wijngaert and Burger, 1986, Gomori, 1952). All reagents for histochemical staining were obtained from a commercial supplier (Sigma Chemical Co., St. Louis, Mo.). A solution of naphthol AS-BI phosphate was prepared by dissolving 25 mg of naphthol AS-BI phosphate in 2.5 ml of n,n-dimethylformamide to which was added 45 ml of 0.05M Tris-maleate buffer (pH 5). A solution of hexazotized pararosanaline was prepared by dissolving 0.25 g of pararosaniline hydroxychloride in 5 ml of distilled water, to which was added 1.25 ml of hydroxychloric acid. This solution was mixed with an equal volume of 4% sodium nitrite immediately before use. The final reaction mixture for histochemical staining was prepared by adding 4 ml of hexazotized pararosanaline solution to the naphthol AS-BI phosphate solution, together with 50 mM sodium-potassium tartrate. The final reaction mixture was filtered before use. Sections were incubated in the reaction mixture at 37° C. for 1 to 2 hours, rinsed in distilled water, counterstained in Mayer hematoxylin, and mounted.

All of the ligament specimens were examined via light microscopy for cells that contained TRAP. A well-defined resorption-modeling surface from the ulna of a young growing rat (Hillam and Skerry, 1995) was used as a positive control. For each batch of slides, a negative control was prepared by omission of the naphthol AS-BI phosphate. Apart from this omission, the negative control slides were handled and prepared in the same manner as the other slides. The negative and positive control slides were reviewed before each batch of slides was analyzed.

Immunohistochemistry: Immunohistochemical staining specific for cathepsin K was performed on frozen sections of all ligament specimens. All incubations were performed in a moist chamber. Endogenous peroxidase activity within frozen sections was quenched by incubation of the slide with a commercial peroxidase blocker (Peroxide Block, InnoGenex, San Ramon, Calif.) at approximately 25° C. (room temperature) for 5 minutes. The slides were rinsed in 0.1M phosphate-buffered saline solution with 0.1% Tween 20 (PBSS-Tween) at pH 7.3 for 5 minutes. Slides were treated with a proteinase solution (Pronase, Biomeda, Foster City, Calif.) for 5 minutes. After proteinase treatment, the slides were rinsed in PBSS-Tween, blocked with casein (Power Block, InnoGenex, San Ramon, Calif.) for 5 minutes at approximately 25° C., rinsed in PBSS with 0.1% bovine serum albumin, and blocked with 5% goat serum in PBSS-Tween for 30 minutes at approximately 25° C. After blocking and further rinsing with PBSS-Tween, the specimens were treated with a mouse monoclonal antibody for cathepsin K (mouse anti-human cathepsin K [clone 182-12G5], Oncogene Research products, San Diego, Calif.) diluted 1:50 with antibody diluent (IHC Kit, InnoGenex, San Ramon, Calif.) and allowed to incubate at 4° C. overnight (minimum of 12 hours).

Following rinsing in PBSS-Tween, the slides were flooded with a biotinylated anti-mouse IgG antibody (IHC Kit, InnoGenex, San Ramon, Calif.) containing 1% canine serum and allowed to incubate for 20 minutes at approximately 25° C. Slides were rinsed in PBSS-Tween and treated with a streptavidin-horseradish peroxidase conjugate (IHC Kit, InnoGenex, San Ramon, Calif.) for 20 minutes at approximately 25° C. After another PBSS-Tween rinse, slides were flooded with an insoluble 3.3'-diaminobenzidine tetrachloride/nickel-cobalt substrate (3,3'-Diaminobenzidine tetrachloride/nickel-cobalt kit, Zymed Laboratories, San Francisco, Calif.) and observed for staining intensity via light microscopy. The slides were rinsed in running water for 5 minutes and counterstained with nuclear fast red (Nuclear Fast Red, Trevigen Inc., Gaithersburg, Md.). Slides were rinsed in running water a final time, dehydrated in increasing concentrations of ethanol, cleared in xylene, and mounted.

All of the ligament specimens were examined via light microscopy for cathepsin K. The resorption-modeling surface from the rat ulna (Hillam and Skerry, 1995) was used as a positive control. For each batch of slides, negative controls were prepared by omission of the primary or secondary antibodies. Apart from these omissions, the negative control slides were handled and prepared in the same manner as the other slides. The negative and positive control slides were viewed via light microscopy before the test slides were reviewed.

Double immunohistochemical-histochemical staining: Ligament specimens also were double-stained for TRAP and cathepsin K. Immunohistochemical staining was performed for cathepsin K as described, except that counterstaining with nuclear fast red was omitted. The same ligament sections then were histochemically stained for TRAP. Negative control sections were prepared as described. Double-stained sections were reviewed qualitatively for cells in which TRAP and cathepsin K were co-localized.

Statistical analyses: The number of cells that contained TRAP or cathepsin K, degree of epiligamentous proliferation, and degree of chondroid metaplasia within the core region of the CCL were scored for each section by use of a 4-category numerical rating scale (negative=0; slightly positive=1; moderately positive=2; strongly positive=3). The Median ANOVA was used to determine whether the number of cells that contained TRAP and cathepsin K in CCL tissue was significantly different in dogs with CCL rupture, compared with aged dogs and young dogs with normal stifle joints. Spearman rank correlations were used to examine associations between lameness duration, epiligamentous proliferation, chondroid metaplasia, localization of TRAP, and localization of cathepsin K in dogs with CCL rupture. Differences were considered significant at $P<0.05$.

Results for Example 1

Twenty-eight of 30 dogs with rupture of the CCL had palpably unstable stifle joints on physical examination and were considered to have complete tears of the CCL. Extensive disruption to the CCL was confirmed at surgery in these dogs. Less extensive disruption to the CCL rupture was confirmed at surgery in the 2 dogs with partial rupture and stable stifle joints. Body weight was 35.5±10.8 kg (mean±SD), and age was 5.2±2.1 years. Median duration of lameness was 2 months, and lameness duration ranged from 3 days to 24 months. One dog was a sexually intact female, 15 dogs were ovariohysterectomized females, 2 dogs were sexually intact males, and 12 dogs were castrated males.

Among the young dogs without CCL rupture, body weight was 10.0±0.7 kg, age was 1.7±0.9 years, and all dogs were sexually intact females. Among the aged dogs without CCL rupture, body weight was 28.8±14.8 kg, age was 10±3.7 years, 5 dogs were ovariohysterectomized females, and 3 dogs were castrated males.

Histologic examination of longitudinal sections of CCL from young unaffected dogs revealed dense regularly orientated connective tissue with parallel bundles of crimped collagen fibers and parallel rows of fusiform ligament fibroblasts. Adjacent to the bone-ligament junction, a thin layer of epiligamentous tissue was evident (FIGS. 1A-1D). Mild chondroid metaplasia was seen in the normal CCL from one (1) dog. Cells that stained for TRAP cells or cathepsin K were not seen in normal CCL of these dogs or in negative control tissues. In the positive control tissues, cells that contained TRAP and cathepsin K were seen on the caudomedial resorption-modeling surface of the rat ulna.

The CCL specimens from the aged dogs without CCL rupture and dogs with CCL rupture had variable numbers of cells that contained TRAP and cathepsin K as well as chondroid metaplasia within the core region of the CCL. A variable amount of epiligamentous proliferation was also seen in dogs with CCL rupture. Chondroid metaplasia was significantly (P=0.005) greater in aged dogs and dogs with CCL rupture, compared with young dogs without CCL rupture. A significant relationship between shorter duration of lameness and the number of cells that contained cathepsin K in ruptured CCL was found.

Figure 2A:
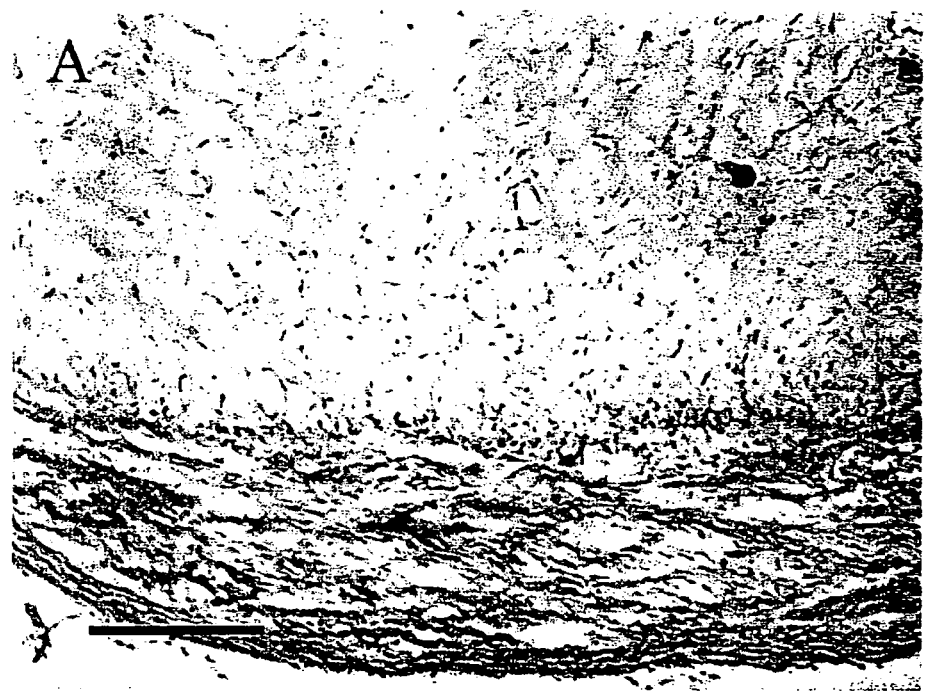
FIGS. 2A, 2B, 2C, and 2D are photomicrographs of longitudinal frozen sections of ruptured human anterior cruciate ligament (FIGS. 2A and 2B) and ruptured canine cranial cruciate ligament (FIGS. 2C and 2D).
Figure 2B:
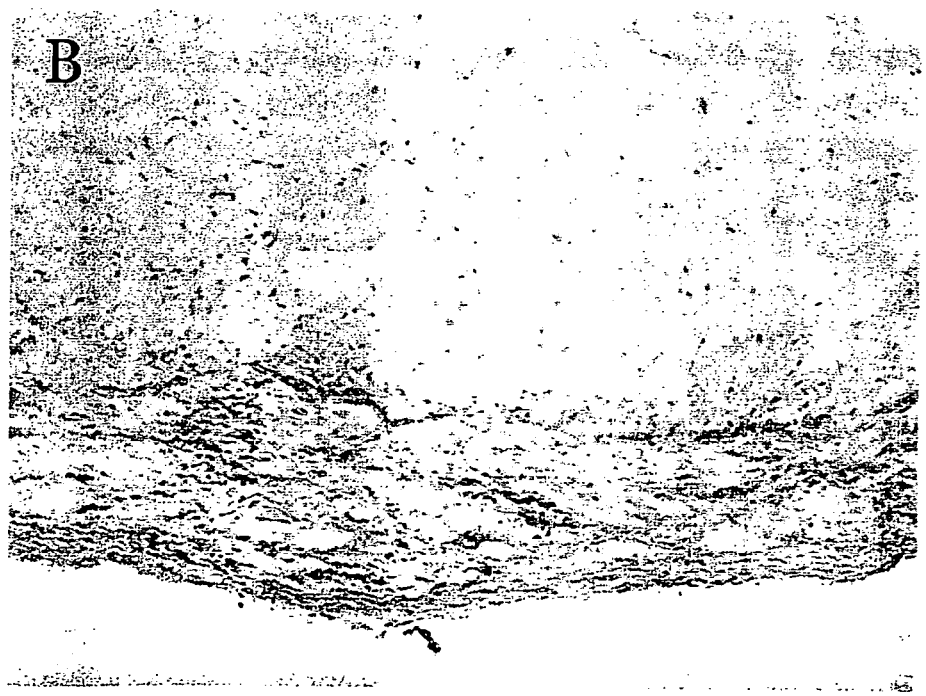
Figure 2C:
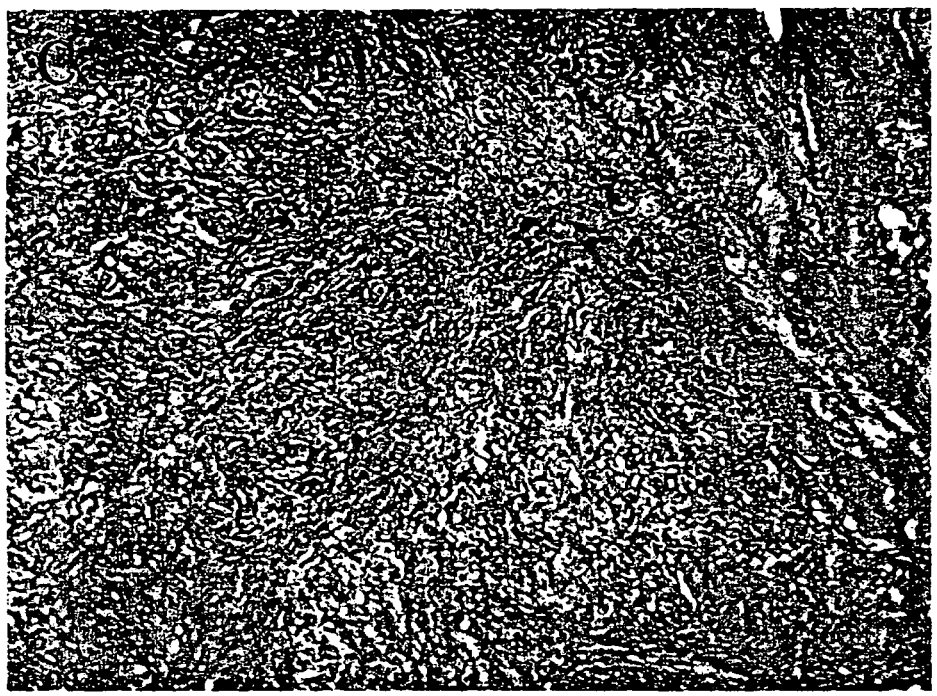
Figure 2D:
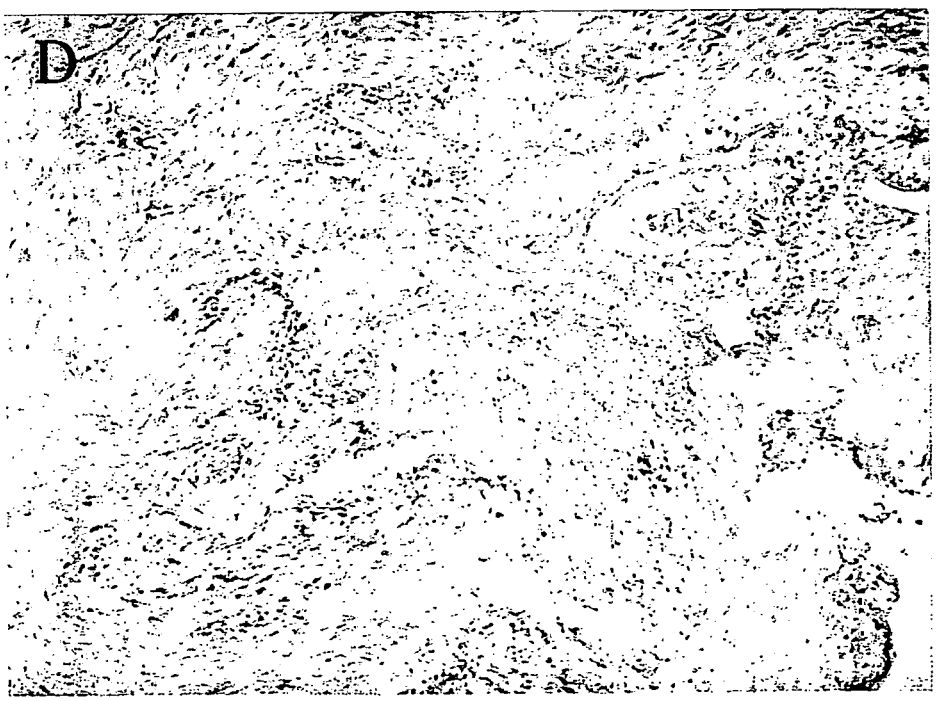
Figure 3:
FIG. 3 is a photomicrograph of a longitudinal section of CCL from a 6-year-old dog without CCL rupture, stained histochemically for TRAP. Small numbers of cells containing TRAP (black arrows), which are often fusiform in shape, are evident within ligament fascicles with matrix degeneration. Fascicles with degenerative changes are interspersed with healthier ligament fascicles, which retain a more organized structure to the matrix collagen, including crimp (white arrows). The separation of the fascicles is an artifact associated with the preparation of frozen sections. Mayer hematoxylin counterstain, bar=100 μm.
Figure 4A:
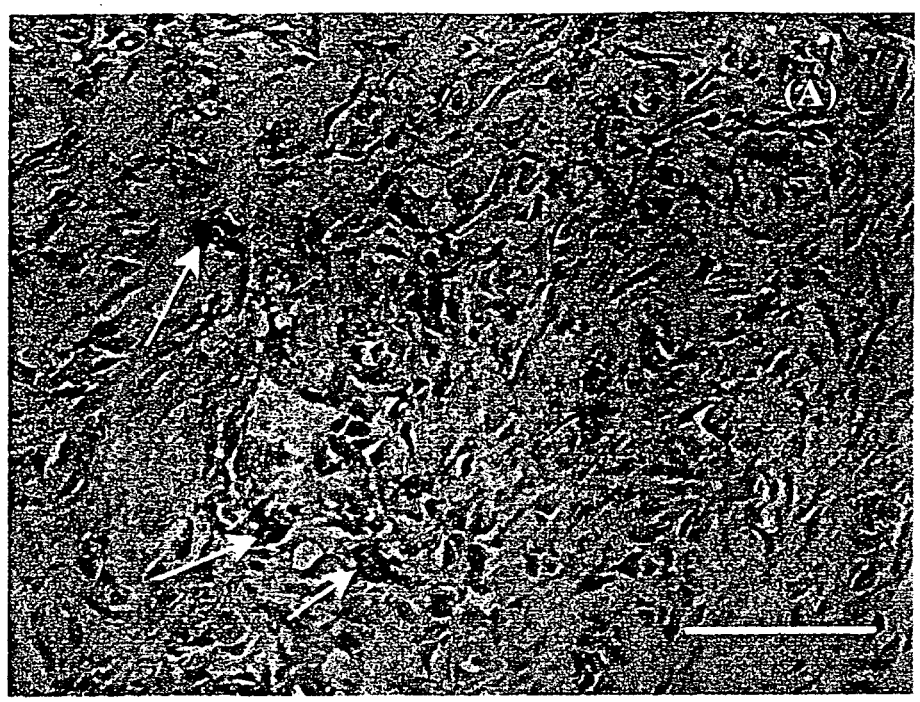
FIGS. 4A and 4B are photomicrographs of longitudinal sections of the epiligamentous region of a ruptured CCL from an 8-year-old dog, stained immunohistochemically for cathepsin K (FIG. 4A) or for cathepsin K and TRAP (FIG. 4B).
Figure 4B:
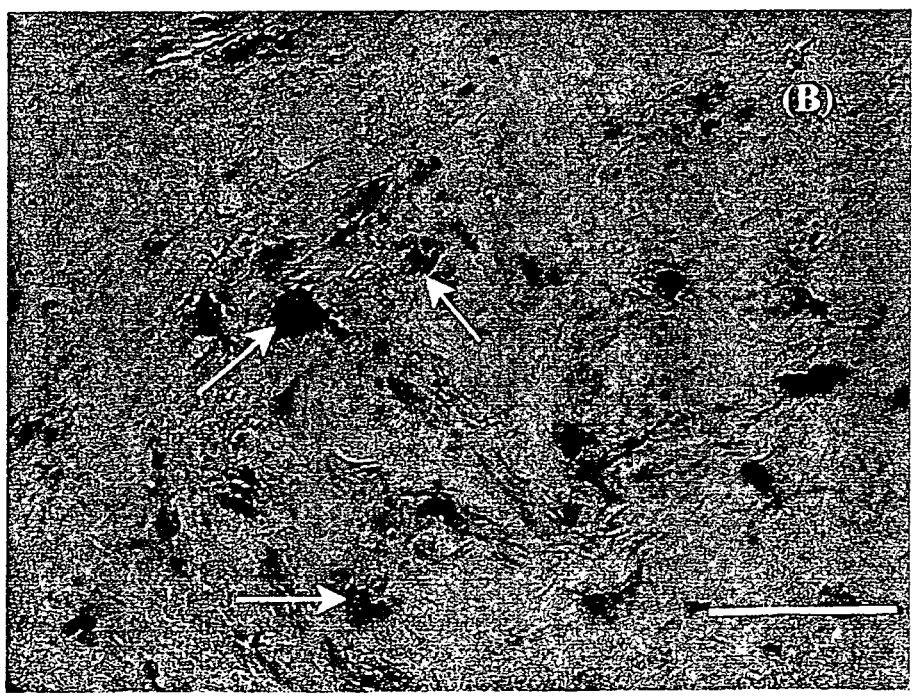
Figure 5:
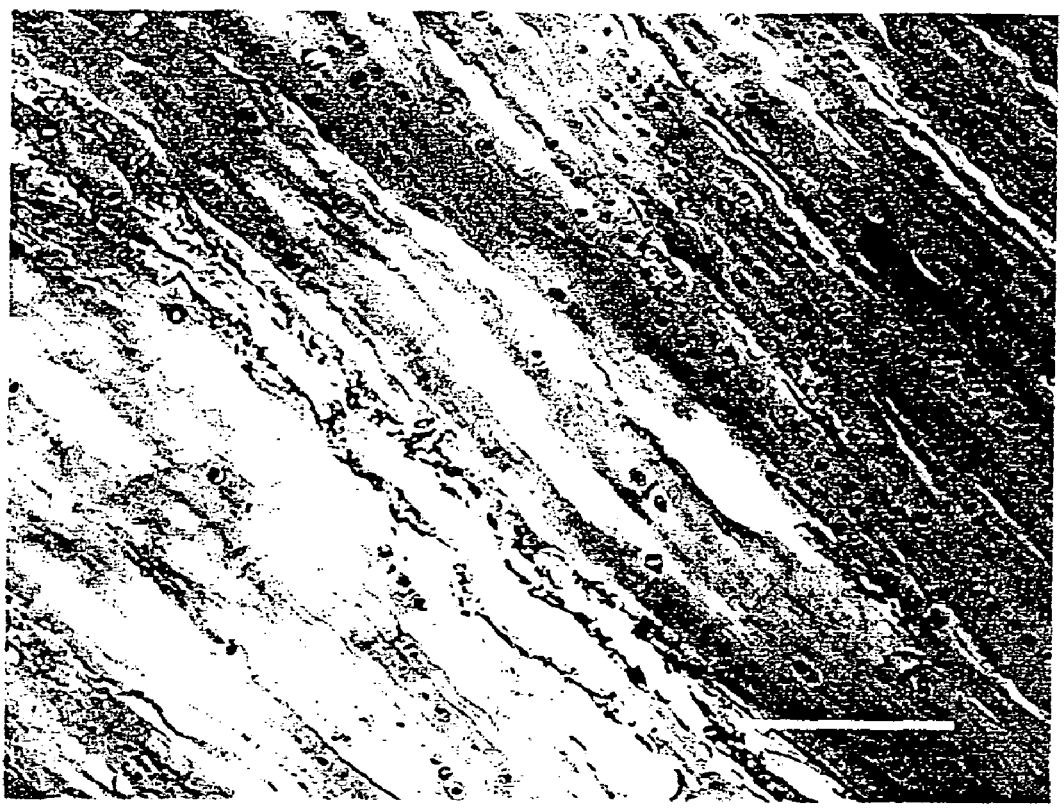
FIG. 5 is a photomicrograph of a longitudinal section of the core region of a ruptured CCL from a 6-year-old dog, stained histochemically for TRAP. Ligament fibroblasts within the core region have undergone transformation to a spheroid phenotype. Clones of the cartilage-like cells also are evident. Little epiligamentous proliferation and TRAP expression are evident in this specimen. Mayer hematoxylin counterstain; bar=200 µm.

The number of cells that contained TRAP and cathepsin K within CCL tissue was significantly greater in dogs with CCL rupture, compared with aged and young dogs that did not have ruptured CCL. The CCL tissue of aged dogs also contained greater numbers of cells that contained TRAP and cathepsin K, compared with young dogs. Many cells that contained TRAP and cathepsin K had a large rounded phenotype quite different from the fusiform phenotype of the ligament fibroblasts (FIG. 2B); similar cells have been observed in humans (FIG. 2C). In dogs with rupture of the CCL, the epiligamentous tissue was much larger in volume and had a high cell number density and blood vessel density, compared with that of dogs without CCL rupture. Cells that contained TRAP and cathepsin K were principally located in the epiligamentous region of the CCL (FIG. 2A), and ligament fascicles within the core region that were adjacent to epiligamentous tissue. In aged dogs without CCL rupture, localization of TRAP and cathepsin K was associated with regions of chondroid metaplasia (FIG. 3). The presence of cells that contained TRAP was positively correlated with the degree of epiligamentous proliferation (P<0.001) and the presence of cathepsin K+ cells (P<0.01; FIG. 4B). Co-localization of cathepsin K in cells that contained TRAP within the CCL was identified in 16 of 25 dogs with CCL rupture (FIG. 4A). Furthermore, epiligamentous proliferation was negatively correlated with chondroid metaplasia within the core region of the CCL (P=0.005; FIG. 5).

EXAMPLE 2

Cathepsin K Activity in Joint Disuse Ligament Degeneration mRNA expression and the activity of cathepsin K in ligaments from ambulatory and unloaded hindlimbs were examined and compared to MMP-2 and MMP-13 levels. Twelve male Sprague-Dawley rats (245±5 grams) were divided into two groups: Ambulatory Control (n=6) and Hindlimb Unloaded (n=6). Hindlimb unloading was performed at the NASA-Ames center to provide a non-invasive model for hindlimb joint disuse (Morey-Holton and Globus, 2002). Animals were prepared by securing the animal in a harness affixed around the tail and raising the harness off the floor of the cage such that the hindlimbs do not touch cage floor. In this arrangement, the forelegs of the animal remain on the ground and afford the animal with mobility around the cage. This "hindlimb-unloading" induces substantial stress reduction by eliminating ground reaction force thereby mimicking joint disuse. Control animals were allowed unrestricted cage movement. All animals were housed at 24° C. under a 12 hour light and 12 hour dark cycle, fed Purina™ rat chow, and watered ad libitum. Rats were checked twice daily for overall health, food and water consumption, and the condition of their tails (the harness should prevent slippage without restricting circulation). After thirty days the animals were euthanized and the medial collateral ligaments of the knee were aseptically harvested and stored in a manner appropriate for their respective experiment.

Real-time quantitative-PCR (RT-QPCR) was performed on six ligaments from each group. During aseptic tissue harvest, the ligaments were briefly rinsed with DNase-, RNase-, and Protease-Free phosphate buffered saline, to remove blood or other contaminants from the tissues, and placed in RNAlater solution (Ambion, Austin, Tex.). During tissue harvest, care was taken not to dissect out the insertion sites of the tissue nor touch the bone in order to reduce potential contamination from bone. RNA isolation was performed using methods similar to that utilized by Reno and co-workers (Reno et al., 1997), which combines the TRIzol™ method with the column fractionation steps of the RNeasy® Total RNA kit (Qiagen Inc., Valencia, Calif.).

Methods primarily followed the manufacturer's instructions for the respective steps. Tissues were pooled to ensure quantifiable RNA. Tissues were placed in a liquid nitrogen cooled Braun Mikro-Dismembrator Vessel (B. Braun Biotech International, Allentown, Pa.) and reduced to powder. One mL of Trizol Reagent (Life Technologies, Grand Island, N.Y.) was added and incubated at room temperature for 5 minutes. The homogenate was then centrifuged to remove insoluble tissue debris, followed by the addition of 0.2 mL of chloroform to the supernate. The samples were mixed vigorously, incubated at room temperature (3 min.), and transferred to a pre-spun 2.0 mL phase lock gel tube (Brinkman-Eppendorf, Westbury, N.Y.). The organic and aqueous phases were then separated by centrifugation at 14,000×g for 5 minutes. Equal volume of 70% EtOH was added to the RNA-containing aqueous phase. Total RNA was then isolated from the ethanol mixture using the column fractionation steps of the RNAeasy Total RNA kit. Yield and purity of RNA were quantified by spectrophotometric measurement at 260, 280, and 325 nm (UltraSpec 3000 Spectrophotometer, Pharmacia Biotech, Cambridge UK). Reverse transcription into cDNA was performed in a 20 µl total volume containing total RNA, 1 µl oligo (dT) (500 ng/µl; Promega, Madison, Wis.), RNase free water, and 9 µl of First Strand Synthesis buffer (Life Technologies) containing 40 units of RNase inhibitor (Ambion), 500 µM dNTP mix, 10 mM DTT, and 200 units of Superscript II reverse transcriptase. Primer sets for rat cathepsin K, MMP-13, and the house keeping gene glyceraldehye-3-phosphate dehydrogenase (GAPDH) were developed and tested for specificity in our laboratory. The primer sets were either derived from previously published reports for MMP-13 (Accession number: M60616, (Knittel et al., 1999), or designed from sequences available from GenBank for cathepsin K (Accession number: AF010306) and GAPDH (Accession number AF106860) using the PrimerSelect module of the Lasergene 5.01 software (DNAStar, Madison, Wis.) and BLAST® (Basic Local Alignment Search Tool).

Primer sequences are MMP-13 forward: 5'-AAA GAA CAT GGT GAC TTC TAC C-3' (SEQ. ID. NO. 1), reverse: 5'-ACT GGA TTC CTT GAA CGT C-3' (SEQ. ID. NO. 2), amplicon length 283 bp; cathepsin K forward: 5'-TGC GAC CGT GAT AAT GTG AAC C-3' (SEQ. ID. NO. 3), reverse:

5'ATG GGC TGG CTG GCT TGA ATC-3' (SEQ. ID. NO. 4), amplicon length 205 bp; and GAPDH forward: 5' GAC TGT GGA TGG CCC CTC TG-3' (SEQ. ID. NO. 5), reverse: 5° CGC CTG CTT CAC CAC CTT CT-3' (SEQ. ID. NO. 6), length 239 bp; MMP-2 forward: GGT CGC AGT GAT GGC TTC CTC T (SEQ. ID. NO. 7); reverse: CAC ACC ACA CCT TGC CAT CGT T (SEQ. ID. NO. 8). Amplicon length 376 bp. Quantitative-PCR standards for each of the genes were prepared from purified PCR products of the target sequences. From spectrophotometric quantitation of the PCR products, the number of copies per µl of each standard was calculated, and ten-fold serial dilutions (ranging from $1\times10^9$ to 10 copies/µL) were prepared. Real-time Q-PCR was performed using a BIO-RAD iCycler iQ Real-time PCR system (BIO-RAD, Hercules, Calif.). All reactions were carried out in a total volume of 20 µL containing IX Platinum Quantitative PCR Supermix (Life Technologies), 10 nM Fluorescein, 200 nM forward primer, 200 nM reverse primer, 0.25× Sybr Green, 5 µl template, and 3.95 µl DEPC-treated H2O at an annealing temperature of 55-60° C. (depending upon the template). Total RNA from bone was used as a positive control, and for negative controls, Superscript II was not included in the reverse transcription reactions. The cDNA copy numbers of the target gene was analyzed after being normalized to the copy number of GAPDH or to the amount of total RNA. Results are shown in FIG. 6.

Figure 8A:
FIGS. 8A, 8B, and 8C are photomicrographs showing immunohistochemical staining for MMP-13 in positive control (FIG. 8A), ambulatory (FIG. 8B), and hindlimb-unloaded MCL tissue (FIG. 8C) (400×). In ambulatory tissues MMP-13 staining was very weak, with only a minor increase in tissues from hindlimb-unloaded animals. No cell counterstaining was done in these samples.
Figure 8B:
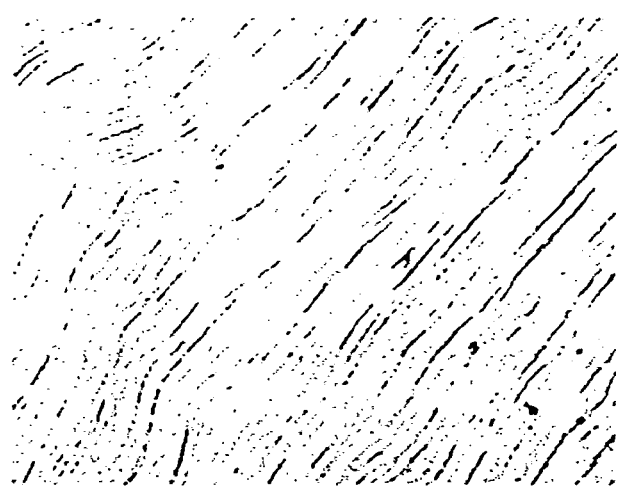
Figure 8C:
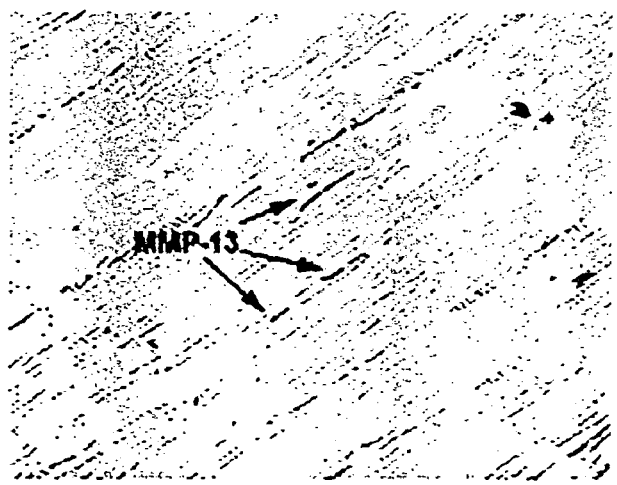

The amount and distribution of cathepsin K and MMP-13 were determined using immunohistochemical techniques. Three MCL specimens from each group were harvested and fixed for 3 days in Zamboni's fixative at 4° C. Fixed ligaments were flash frozen in Optimal Cutting Temperature Media (OCT) at –70° C., cryosectioned (approximately 6 □m) and mounted onto lysine-coated slides. Mounted specimens were washed in a solution of phosphate buffered saline and 0.1% Tween-20 (PBST) between all of the following incubation steps. Specimens were incubated with peroxide solution and blocked with serum (specific to host species of primary antibody) using a commercially available kit (Innogenex Rodent IHC Kit, San Ramon, Calif.). Specimens were then incubated overnight with primary antibody (Chemicon, Temecula, Calif.) for either cathepsin K (FIGS. 7A-7F) or MMP-13 (FIGS. 8A-8C). Following incubation with primary antibody, samples were incubated with biotinylated goat anti-mouse secondary antibody, peroxidase solution (HRP), and stained with diaminobenzidine (DAB). At least four sections were obtained per tissue and positive cells counted within the section and normalized by tissue area. Bone tissue was used as a positive control for cathepsin K while carcinoma slides (provided by the manufacturer) were used as positive control for MMP-13 (FIG. 9). Negative controls were obtained by omitting primary antibody from the protocol.

Determination of Enzyme Activity: The enzyme activity of cathepsin K was determined in three specimens per group by measuring the rate of hydrolysis of the Z-Leu-Arg-7-amino-4-methylcourmarin (Z-Leu-Arg-AMC) substrate (MD Biosciences, Montreal, Canada). After dissection (again care was taken not to include insertion sites or bone tissue), tissues were homogenized and placed in buffer (50 mM Potassium Phosphate, pH 6.5, 2.5 mM DTT, and 2.5 mM $Na_2EDTA$). Substrate hydrolysis was monitored in tissues from control and hindlimb-unloaded animals and fluorescent AMC standards at room temperature in a SpectraMax Gemini Dual-Scanning Spectrofluorometer (Molecular Devices, Sunnyvale, Calif.) plate reader. Bone was used as a positive control and omitting the tissue homogenate or the substrate provided negative controls. Relative fluorescence was converted to enzyme activity units following the manufacturer's instructions. One unit of enzyme activity is the amount of enzyme that cleaves one micromole of AMC per minute, per milliliter. Enzyme activity was normalized by tissue weight.

Statistical analysis was performed using an unpaired (two-group) t-test. The level of significance was set to be 0.05. Results are shown in FIG. 10.

Results for Example 2

No treatment complications were present in the hindlimb-unloaded animals. Quantitative PCR analyses for cathepsin K and MMP-13 reveal substantial changes in gene expression between tissues from ambulatory control and hindlimb-unloaded animals. Hindlimb unloading resulted in increased cathepsin K and MMP-13 mRNA levels (FIG. 6). Cathepsin K levels increased greater than three fold in hindlimb-unloaded tissues while MMP-13 levels in hindlimb-unloaded tissue increased by approximately thirty fold. However, cathepsin K levels were substantially larger than MMP-13 levels in both ambulatory and hindlimb-unloaded tissues with considerably larger cathepsin K mRNA levels in tissue subjected to disuse. Immunohistochemical examination of cathepsin K staining revealed the presence of the enzyme in tissues from both ambulatory and hindlimb-unloaded animals (FIGS. 7A-7F). Cathepsin K staining appeared more extensive in disuse tissues (FIGS. 7D, 7E and 7F) which also showed signs of increased extracellular matrix disorganization. In tissues from ambulatory animals (FIGS. 7A, 7B, and 7C), cathepsin K staining was present in spindle shaped cells aligned between collagen fibers as is characteristic of fibroblasts. In ligaments from hindlimb-unloaded animals, staining was also present in cells showing the characteristics of fibroblasts but also appeared in cells with a more rounded appearance. Ligaments from ambulatory animals (FIG. 8B) showed very weak and diffuse staining for MMP-13 with minor increases in staining in hindlimb-unloaded tissues (FIG. 8C) while positive controls were positive (FIG. 8A). Quantitative analysis of the number of positively stained cathepsin K or MMP-13 cells revealed substantial increases in cathepsin K staining in tissues from hindlimb-unloaded animals and followed the same trend as gene expression findings (FIG. 9). MMP-13 staining also increased during disuse but not as dramatically as cathepsin K. In addition, cathepsin K staining was much more numerous than MMP-13 staining in ambulatory animals. Cathepsin K enzyme activity was significantly increased by tissue disuse. Enzyme activity was approximately five fold greater in ligaments from hindlimb-unloaded animals when compared to ambulatory control animals (FIG. 10).

EXAMPLE 3

Identification of Proteases Associated with Synovitis

In order to investigate the extent of protease infiltration into the joint capsule and its correlation with ligament degeneration, samples of synovial membrane and ruptured CCL were taken from the same population (n=15) of dogs and prepared histologically as described in Example 1.

Specimen collection and preparation: Remnants of ruptured CCL and synovial membranes were excised from the femoral and tibial attachment sites in affected dogs. Immediately after collection, ligament and synovial membrane specimens were placed in tissue cassettes and fixed in Zamboni fixative (Stefani et al., 1967) for 1 to 2 days at 4° C. Frozen sections, 10 µm thick, were cut and mounted on glass slides for histologic examination. Multiple slides were created from each specimen for histochemical and immunohistochemical staining, in addition to staining with H&E.

Histochemistry: Histochemical staining specific for TRAP was performed on all ligament specimens, and was based on established methods (Van de Wijngaert and Burger, 1986, Gomori, 1952). All reagents for histochemical staining were obtained from a commercial supplier (Sigma Chemical Co., St. Louis, Mo.). A solution of naphthol AS-BI phosphate was prepared by dissolving 25 mg of naphthol AS-BI phosphate in 2.5 ml of n,n-dimethylformamide to which was added 45 ml of 0.05M Tris-maleate buffer (pH 5). A solution of hexazotized pararosanaline was prepared by dissolving 0.25 g of pararosaniline hydroxychloride in 5 ml of distilled water, to which was added 1.25 ml of hydroxychloric acid. This solution was mixed with an equal volume of 4% sodium nitrite immediately before use. The final reaction mixture for histochemical staining was prepared by adding 4 ml of hexazotized pararosanaline solution to the naphthol AS-BI phosphate solution, together with 50 mM sodium-potassium tartrate. The final reaction mixture was filtered before use. Sections were incubated in the reaction mixture at 37° C. for 1 to 2 hours, rinsed in distilled water, counterstained in Mayer hematoxylin, and mounted.

All of ligament and synovial membrane specimens were examined via light microscopy for cells that contained TRAP. A well-defined resorption-modeling surface from the ulna of a young growing rat (Hillam and Skerry, 1995) was used as a positive control. For each batch of slides, a negative control was prepared by omission of the naphthol AS-BI phosphate. Apart from this omission, the negative control slides were handled and prepared in the same manner as the other slides. The negative and positive control slides were reviewed before each batch of slides was analyzed.

Immunohistochemistry: Immunohistochemical staining specific for cathepsin K was performed on frozen sections of all ligament and synovial membrane specimens. All incubations were performed in a moist chamber. Endogenous peroxidase activity within frozen sections was quenched by incubation of the slide with a commercial peroxidase blocker (Peroxide Block, InnoGenex, San Ramon, Calif.) at approximately 25° C. (room temperature) for 5 minutes. The slides were rinsed in 0.1M phosphate-buffered saline solution with 0.1% Tween 20 (PBSS-Tween) at pH 7.3 for 5 minutes. Slides were treated with a proteinase solution (Pronase, Biomeda, Foster City, Calif.) for 5 minutes. After proteinase treatment, the slides were rinsed in PBSS-Tween, blocked with casein (Power Block, InnoGenex, San Ramon, Calif.) for 5 minutes at approximately 25° C., and blocked with 5% goat serum in PBSS-Tween for 30 minutes at approximately 25° C. After blocking and further rinsing with PBSS-Tween, the specimens were treated with a mouse monoclonal antibody for cathepsin K (mouse anti-human cathepsin K [clone 182-12G5], Oncogene Research products, San Diego, Calif.) diluted 1:50 with antibody diluent (IHC Kit, InnoGenex, San Ramon, Calif.) and allowed to incubate at 4° C. overnight (minimum of 12 hours).

Following rinsing in PBSS-Tween, the slides were flooded with a biotinylated anti-mouse IgG antibody (IHC Kit, InnoGenex, San Ramon, Calif.) containing 1% canine serum and allowed to incubate for 20 minutes at approximately 25° C. Slides were rinsed in PBSS-Tween and treated with a streptavidin-horseradish peroxidase conjugate (IHC Kit, InnoGenex, San Ramon, Calif.) for 20 minutes at approximately 25° C. After another PBSS-Tween rinse, slides were flooded with an insoluble 3.3'-diaminobenzidine tetrachloride/nickel-cobalt substrate (3,3'-Diaminobenzidine tetrachloride/nickel-cobalt kit, Zymed Laboratories, San Francisco, Calif.) and observed for staining intensity via light microscopy. The slides were rinsed in running water for 5 minutes and counterstained with nuclear fast red (Nuclear Fast Red, Trevigen Inc., Gaithersburg, Md.). Slides were rinsed in running water a final time, dehydrated in increasing concentrations of ethanol, cleared in xylene, and mounted.

All of the ligament and synovial membrane specimens were examined via light microscopy for cathepsin K. The resorption-modeling surface from the rat ulna (Hillam and Skerry, 1995) was used as a positive control. For each batch of slides, negative controls were prepared by omission of the primary or secondary antibodies. Apart from these omissions, the negative control slides were handled and prepared in the same manner as the other slides. The negative and positive control slides were viewed via light microscopy before the test slides were reviewed.

Results for Example 3

Figure 11A:
FIGS. 11A and 11B are photomicrographs of sections of synovial membrane from a dog with cranial cruciate ligament rupture.
Figure 11B:
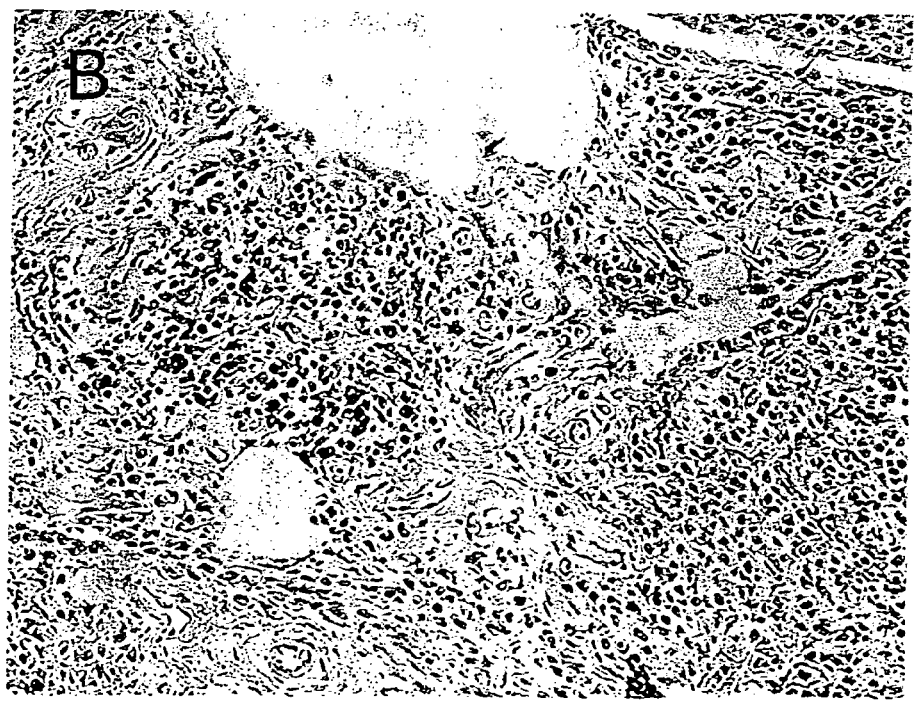

Of the 15 dogs having ruptured CCL, 9 showed positive staining for TRAP in cells that had infiltrated the synovial membrane as shown in FIG. 11A. Of those same 15 dogs, 4 had positive staining for cathepsin K in cells that had infiltrated the synovial membrane, as illustrated in FIG. 11B. For this same population, 10 of 15 had positive TRAP staining in cells from the ruptured CCL (not shown), while 3 of 15 had cells, which stained positive for cathepsin K in the ruptured CCL (not shown). Slides of the synovial membrane also show extensive infiltration by mononuclear leukocytes, cells intimately associated with the inflammatory process. These results indicate that the degenerative processes unmasked in ligaments and described in Examples 1 and 2 are, generally, mirrored by events occurring in the synovial membrane. In addition, these results indicate that cathepsin K expressing cells may not be limited to fibroblasts as previously thought but may also be expressed by leukocytes responding to the inflammatory response. Thus, the effects observed in ligament degeneration can be extrapolated to other structures of the joint. This information is important in approaching treatment of other structures in the joint that are affected by degenerative processes as well.

EXAMPLE 4

Diagnosing Joint Disease Using PCR to Measure Cathepsin K Gene Expression

Total RNA was isolated from canine joint fluid using Trizol reagent (Invitrogen, Carlsbad, Calif., #10296010) and cleaned with Qiagen's RNeasy mini kit (Qiagen, Valencia, Calif., #74106). cDNA was generated from 10 µl of total RNA by using the superscript first-strand synthesis system for RT-PCR kit from Invitrogen (#11904018). The primers were designed by QIAGEN. The optimal PCR conditions determined were: annealing temperature 55° C. for 30 seconds, extension at 72° C. for 90 seconds, denaturing at 94° C. for 30 seconds for a total of 30 cycles. A 578 bp fragment of cathepsin K was amplified using the primers: forward 5'-CAGT-GTGGTTCCTGTTGGGCTTT-3' (SEQ. ID. NO. 9) and reverse 5'-TCACATCTTGGGGAAGCTGG-3' (SEQ. ID. NO. 10). PCR products were analyzed on 1.2% agarose gel electrophoresis using ethidium bromide staining and UV light visualization.

Extraction of total RNA from Joint fluid: 750 µl of Trizol reagent (Invitrogen, Carlsbad, Calif.) and 250 µl of joint fluid were incubated at room temperature (RT) for 5 minutes and then added 200 µl of chloroform (Sigma) was added and the mixture shaken vigorously by hand for 15 seconds followed by incubation at RT for 10 min. The mixture was then centrifuged at 4° C., 12000 rpm for 15 minutes. The aqueous phase (upper) was then transferred to a new micro tube, to which was added 500 µl of isopropyl alcohol (2-propanol, Fisher Scientific) into the new tube. The contents of the tube were mixed and incubated at RT for 10 min. followed by centrifugation at 4° C., 12,000 rpm for 10 minutes. The supernatant was discarded and the pellet washed with 1 ml of 75% EtOH and centrifuged at 4° C., 8,600 rpm for 5 minutes. The supernatant was discarded and the pellet allowed to air dry for 10 minutes at room temperature. The RNA containing pellet was redissolved in 100 µl of RNase-free water.

Cleaning total RNA: Total RNA was cleaned using the Qiagen RNeasy system (Qiagen, Cat. No. 74124), according to manufacturers instructions. Briefly, 350 µl of buffer RLT was added to the pellet and mixed, by 250 µl of 100% EtOH was then added and mixed by pipetting. The entire sample was transferred to an RNeasy column and centrifuged for 15 sec. Following centrifugation, 350 µl of RW1 buffer was layered onto the column and centrifuged for 15 seconds. Eighty (80) µl of a mixture of 10 µl of DNase and 70 µl of RDD buffer were then added into the column. The column was then incubated at room temperature for 15 minutes. Following incubation 350 µl of RW1 buffer was added to the column followed by centrifugation at 12,000 rpm for 15 seconds. The RNeasy column was then transferred to a new 2 ml collection tube to which was added 500 µl of buffer RPE. The column was then centrifuged at 12,000 rpm for 2 minutes. The RNeasy column was then transferred to a new 1.5 ml collection tube to which was added 30 µl of RNase-free water, the tube centrifuged for 1 minute at 12,000 rpm and samples containing the eluted RNA were collected and stored at −80° C.

RT-PCR-RNA to cDNA: All reagents were mixed for a total volume 12 µl: 10 µl of total RNA, 1 µl of 10 mM dNTP mix, 1 µl of 0.5 ng/µl of Oligo (dT12-18). The mixture was then incubated at 65° C. in a heating block for 5 minutes. The tube was then placed on ice for at least 1 min. to which was then added 2 µl of 10×Rt buffer, 25 mM $MgCl_2$, 2 µl of 0.1 MDTT and 1 µl of RNase out inhibitor. The contents of the tube were then mixed gently and incubated at 42° C. in a water bath for 2 minutes. After incubation, 1 µl of superscript II RT was added to each test tube, excluding the control tube. The tubes were then flicked to gently mix the contents and incubated at 42° C. in a water bath for 50 minutes followed by incubation at 70° C. in a heat block for 15 minutes to terminate the reaction. The tubes containing the samples were then placed on ice. The tubes were then centrifuged briefly and 1 µl of RNase H was added to all the tubes followed by incubation at 37° C. in water bath for 20 minutes and placed on ice.

PCR: All PCR reactions were carried out in a final volume of 50 µl and contained 5 µl of 10×Mg free water, 1.5 µl of 50 mM of $MgCl2$, 1 µl of 10×dNTPs, 1 µl of 250 M forward primers, 1 µl of 250 µM reverse primer, 1 µl of cDNA and 0.25 µl of Taq enzyme. The mixture was incubated for 2 minutes at 94° C. and subjected to 30 cycles of amplification at the following conditions: annealing temperature 55° C. for 30 seconds; extension at 72° C. for 90 seconds; and denaturing at 94° C. for 30 seconds.

Results for Example 4

Control experiments using the above protocols were performed on two sets of tissues. One set comprised ruptured cranial cruciate ligament (RCCL) and one set comprised synovial fluid (SF). In addition, as a control for spurious priming of either the genomic copy or non-homologous sequences, each protocol was performed with and without the presence of reverse transcriptase. The results shown in FIG. 12 show products of the predicted size for both tissues only in the presence of reverse transcriptase, indicating that the template must be mRNA, which first requires conversion into cDNA to allow the PCR reaction to proceed. Following the positive control experiments, 8 dogs showing clinical symptoms of stifle lameness were tested. Four of the animals had positive PCR results for cathepsin K in the synovial fluid while four did not show any product as shown in FIG. 13. These results indicate that in at least half the cases of clinically diagnosed degenerative ligament disease, diagnosis can be made from a sample of the synovial fluid. This relatively non-traumatic means of tissue sampling provides a method for the specific diagnosis of degenerative ligament disease by identifying the cathepsin K message in samples of synovial fluid.

EXAMPLE 5

Inhibition of Cathepsin K Activity

Cathepsin K Inhibition Assay: The cathepsin K inhibition assay was modified from a previously described protocol (Votta et al., 1997). Doxycycline, tetracycline and minocycline were dissolved in 0.1 M Tris/0.15M NaCl buffer, pH 7.4. COL-3 was dissolved in 100% ethanol. NPI-3469 was dissolved in dimethylsulphoxide. Ten microliters of doxycycline, tetracycline, minocycline, COL-3, and NPI-3469 were dissolved in buffer and an equal volume of 0.125 µM rh-human cathepsin K standard dissolved in 100 mM sodium acetate buffer, pH 5.5 were mixed in a 96-well microplate and incubated at approximately 25° C. (room temperature) for 15 minutes.

Concentrations of the candidate inhibiting compound in the initial mixture were prepared at 10-7 to 10-3M. Then 180 µl of an MCA substrate buffer containing 100 mM sodium acetate buffer pH 5.5, 2.5 mM dithiothreitol, 2.5 mM EDTA, and 5 µM Z-Gly-Pro-Arg-MCA substrate (Peptides International, Louisville, KY) was added to the mixture. The microplate was incubated for 60 minutes at approximately 25° C. The fluorescence of each well was then determined using a fluorescent microplate reader set at 360 nm excitation/460 nm emission.

Matrix Metalloproteinase-2 Inhibition Assay: The matrix metalloproteinase-2 (gelatinase A) inhibition assay used a commercially available kit (ECM700 MMP Gelatinase Activity Assay Kit, Chemicon International, Temecula, Calif.). Twenty-five microliters (25 µl) of doxycycline, tetracycline, minocycline, Col-3, NPI-3469 dissolved in buffer as previously described and an equal volume of 100 ng/ml MMP-2 standard dissolved in sample diluent buffer were mixed in a 96-well microplate and incubated at approximately 25° C. for 15 minutes. Concentrations of the candidate inhibiting compounds in the initial mixture were prepared at 10-7 to 10-3M. Then 100 µl of biotinylated gelatinase substrate was added to the mixture for 30 minutes at 37° C. After washing the microplate three times with washing buffer, 100 µl of streptavidin-enzyme conjugate was added to each well and the microplate was incubated at 37° C. for 30 minutes. The microplate was again washed three times with washing buffer and 100 µl of stop buffer was added to each well. After 100 µl of substrate buffer was added to each well, the microplate was incubated at approximately 25° C. for 20 minutes and the optical density of each well was measured at 450 nm using a microplate reader.

Matrix Metalloproteinase-13 Inhibition Assay: The MMP-13 (collagenase 3) inhibition assay used a commercially available kit (Chondrex, Inc., Redmond, Wash., Cat. No. 3003) The recombinant human MMP-13 (collagenase 3) was activated by adding 5 µl of a 10 µg/ml solution of recombinant human MMP-13, 90 µl of sample dilution and reaction buffer (Solution B), and 5 µl of p-aminophenylmercuric acetate to each well of a microplate. The microplate was then incubated for 60 minutes at 35° C. Ten microliters of proteinase inhibitor was then added to each well to neutralize non-collagenolytic proteases in the sample solutions. Twenty five microliters of doxycycline, tetracycline, minocycline, COL-3, NPI-3469 (dissolved in buffer as previously described) and 25 µl of solution B were added to each well. Concentrations of the candidate inhibiting compounds in the initial mixture were prepared at $10^{-7}$ to $10^{-3}$ M using solution B. After the microplate was incubated at approximately 25° C. for 30 minutes, 10 µl of stop solution was added to each well and the fluorescence of each well was then determined using a fluorescent microplate reader set at 360 nm excitation/460nm emission.

Tartrate-resistant Acid Phosphatase Inhibition Assay: The tartrate-resistant acid phosphatase assay was modified from a previously described protocol (Lang et al., 2001). Fifty microliters of doxycycline, tetracycline, minocycline, COL-3, and NPI-3469 dissolved in buffer as previously described and an equal volume of 6.25 mU/ml of tartrate-resistant acid phosphatase standard in phosphate buffered saline were mixed in 96-well microplate and incubated at approximately 25° C. for 15 minutes. Then 50 µl of substrate buffer containing 0.2 M sodium acetate buffer, 0.4 M potassium chloride, 20 mM of sodium tartrate, 2 mM ascorbic acid, 200 µM of ferric chloride, and 2.5 mM of p-nitrophenylphosphate was added to the mixture. Concentrations of the candidate inhibiting compounds in the initial mixture were prepared at $10^{-7}$ to $10^{-3}$ M. The microplate was incubated at 37° C. for 60 minutes. The reaction was stopped by adding 50 µl of 0.9M NaOH, and the optical density of each well was measured at 405 nm using a microplate reader.

Data Analysis: The residual collagenolytic enzyme activity as a percentage of the control was calculated for each concentration of each inhibiting compound. All dilutions of each inhibiting compound were assayed in duplicate and a mean value was calculated for each well.

Results for Example 5

Figure 14:
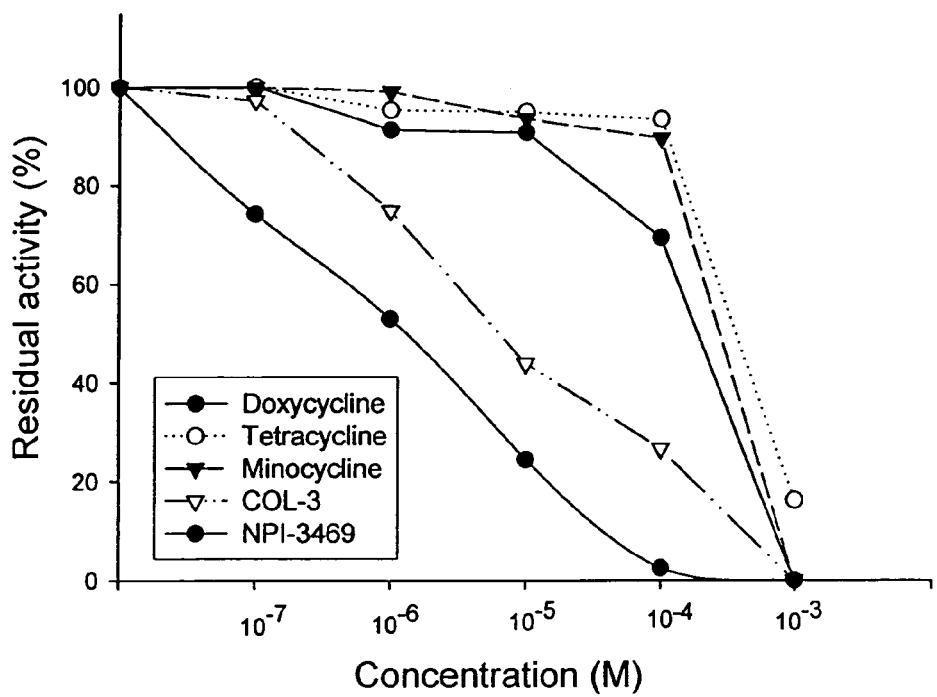
FIG. 14 is a graph illustrating in vitro inhibition of cathepsin K by NPI-3469, COL-3, and various tetracycline compounds. The concentrations of each compound in the initial reaction mixture are shown on the x-axis.

Inhibition of Cathepsin K: To investigate the inhibitory effect of COL-3, NPI-3469, and the various tetracycline compounds on cathepsin K activity, recombinant human cathepsin K was incubated with various concentrations of doxycycline, tetracycline, minocycline, COL-3, and NPI-3469, and the enzyme residual activity was measured with a labeled peptide substrate. At 1 mM concentrations, all the compounds except tetracycline inhibited cathepsin K completely. However, at lower concentrations, more potent inhibition was seen with NPI-3469 and COL-3, compared with the other tetracycline compounds. NPI-3469 inhibited cathepsin K 47% at 1 µm and 75% at 10 µm. COL-3 inhibited cathepsin K 25% at 1 µm and 56% at 10 µm. Little inhibition of cathepsin K was seen with the other tetracycline compounds at concentrations below 100 µm (FIG. 14).

Figure 15:
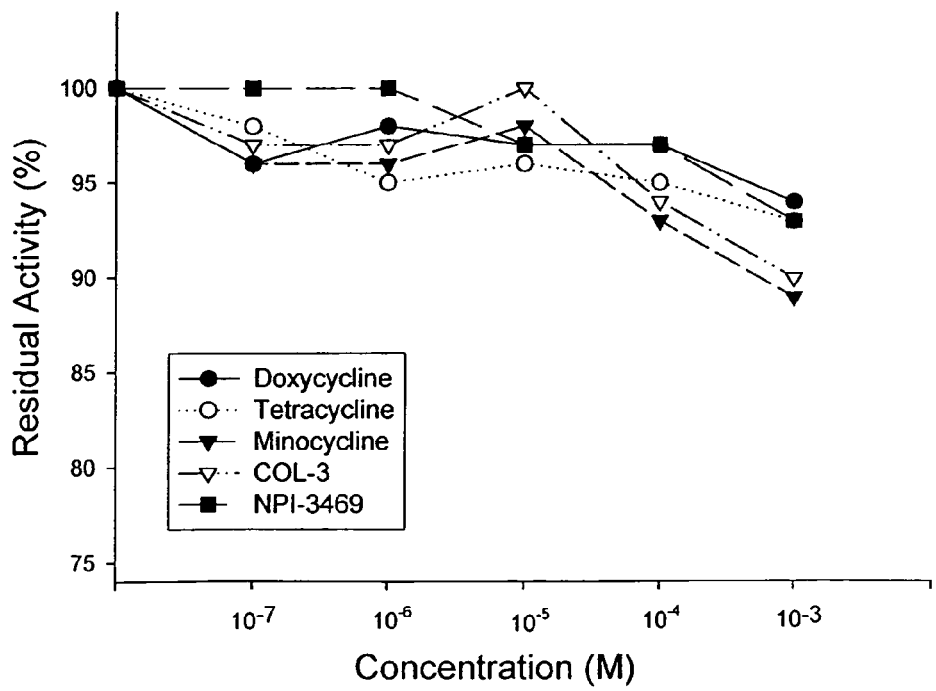
FIG. 15 is a graph illustrating the in vitro inhibition of matrix metalloproteinase-2 (gelatinase A) by NPI-3469, COL-3, and various tetracycline compounds. The concentrations of each compound in the initial reaction mixture are shown on the x-axis.

Inhibition of Matrix Metalloproteinase-2: To investigate the inhibitory effect of COL-3, NPI-3469, and the various tetracycline compounds on matrix metalloproteinase-2 (gelatinase A) activity, matrix metalloproteinase-2 was incubated with various concentrations of doxycycline, tetracycline, minocycline, COL-3, and NPI-3469, and the enzyme residual activity was measured with a labeled collagen substrate. At 1 mM concentrations, less than 10% inhibition was seen with all compounds. At lower concentrations very little inhibition was seen with any of the compounds and below 100 µm, less than 5% of the matrix metalloproteinase-2 activity was inhibited (FIG. 15).

Figure 16:
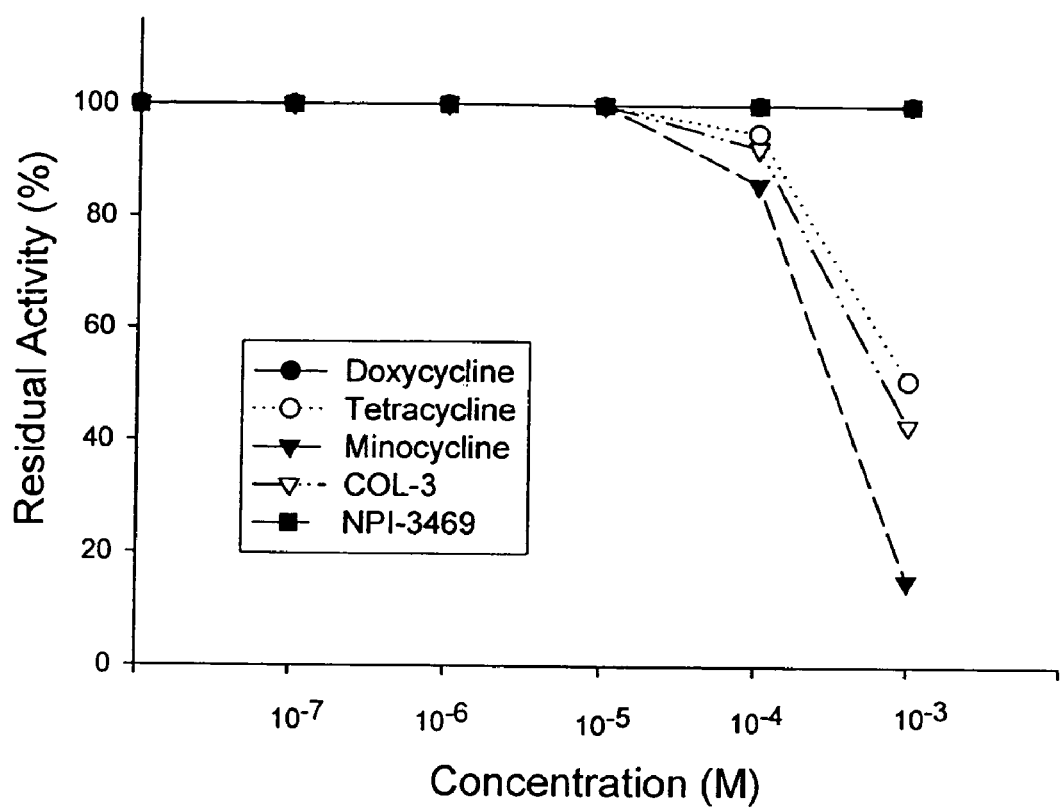
FIG. 16 is a graph illustrating the results of the in vitro inhibition of matrix metalloproteinase-13 (collagenase 3) by NPI-3469, COL-3, and various tetracycline compounds. The concentrations of each compound in the initial reaction mixture are shown on the x-axis.

Inhibition of Matrix Metalloproteinase-13: To investigate the inhibitory effect of COL-3, NPI-3469, and the various tetracycline compounds on matrix metalloproteinase-13 (collagenase 3) activity, matrix metalloproteinase-13 was incubated with various concentrations of doxycycline, tetracycline, minocycline, COL-3, and NPI-3469, and the enzyme residual activity was measured with a labeled collagen substrate. At 1 mM concentrations, inhibition was variable and was most pronounced with minocycline. Inhibition of 85% was seen with minocycline, 57% inhibition with COL-3, and 49% inhibition with tetracycline. Doxycycline and NPI-3469 did not inhibit matrix metalloproteinase-13. At concentrations below 1 mM, little inhibitory activity was seen with any compound (FIG. 16).

Inhibition of Tartrate-Resistant Acid Phosphatase: To investigate the inhibitory effect of COL-3, NPI-3469, and the various tetracycline compounds on tartrate-resistant acid phosphatase activity, tartrate-resistant acid phosphatase was incubated with various concentrations of doxycycline, tetracycline, minocycline, COL-3, and NPI-3469, and the enzyme residual activity was measured with an enzyme substrate. No inhibition of tartrate-resistant acid phosphatase was observed with any compound.

EXAMPLE 6

Involvement of Cathepsin S and TRAP in Diagnosing Joint Disease and PCR Assay Therefor In addition to the RT-PCR assays carried out to monitor the expression of the genes described in Examples 2 and 4, an assay directed to expression of another gene, cathepsin S, was developed. Expression of cathepsin S is tissue-specific and has a specific role in antigen processing by dendritic cells and macrophages [Nakagawa et al 1999]. The level of cathepsin S expression can influence the severity of auto-immune collagen-induced arthritis [Nakagawa et al 1999]. Therefore, inhibition of cathepsin S may reduce the severity of immune response in joints affected with inflammatory arthropathy.

Qualitative RT-PCR assays were carried out to study mRNA expression in ruptured and intact CCL tissue collected from young (1-2 years) normal and aged (3-5 years) normal dogs for the following genes: cathepsin K, cathepsin S, TRAP, MMP-1, MMP-2, MMP-3, MMP-9, and MMP-13.

The primers used in this study were as follows:

TRAP primers:
primer 1 (forward primer), 5' CAGCTGTCCTGGCTCAA 3' (SEQ ID NO: 11)
primer 2 (reverse primer), 5' TAGCCGTTGGGGACCTT 3' (SEQ ID NO: 12) Cathepsin K primers:
primer 1 (forward primer), 5' CAGTGTGGTTCCTGT-TGGGCTTT 3' (SEQ ID NO:9)
primer 2 (reverse primer), 5' TCACATCTTGGG-GAAGCTGG 3' (SEQ ID NO: 10)
Cathepsin S primers:
primer 1 (forward primer), 5' CGTCTCATCTGG-GAAAAGAA 3' (SEQ ID NO: 13)
primer 2 (reverse primer), 5'GCTTTGTAGGGATAG-GAAGC 3' (SEQ ID NO: 14)
MMP-1 primers:
primer 1 forward primer), 5' TTCGGGGAGAAGTGAT-GTTC 3' (SEQ ID NO:15)
primer 2 (reverse primer), 5'GCAGTTGAACCAGC-TATTAGC 3' (SEQ ID NO:16)
MMP-2 primers:
primer (forward primer), 5' ATGGCAAATACGGCT-TCTGC 3' (SEQ ID NO:17)
primer (reverse primer), 5' TGCAGCTCTCATGCT-TGTTG 3' (SEQ ID NO:18)

MMP-3 primers:
   primer (forward primer), 5' ACAGTGGTCCTGTCGT-TGAA 3' (SEQ ID NO: 19)
   primer (reverse primer), 5' AGTCACCTCCTTCCAGA-CAT 3' (SEQ ID NO:20)
MMP-9 primers:
   primer (forward primer), 5' CGCTATGGCTACACT-CAAGT 3' (SEQ ID NO:21)
   primer (reverse primer), 5' AAGTGATGTCGTTGTG-GTGC 3' (SEQ ID NO:22)
MMP-13 primers:
   primer (forward primer), 5' CTGAGGAAGACTTC-CAGCTT 3' (SEQ ID NO:23)
   primer (reverse primer), 5' TTGGACCACTTGAGAGT-TCG 3' (SEQ ID NO:24)
GAPDH Primers:
   Primer (Forward primer) 5'ACCACAGTCCATGCCAT-CAC 3' (SEQ ID NO:25)
   Primer (Reverse primer) 5'TCCACCACCCTGTTGCT-GTA 3 (SEQ ID NO:26)

The RT primer used was oligo (dT) from a kit (Invitrogen, cat. No: 18080-051) PCR reaction conditions were as follows and as described for the cathepsin K RT-PCR assay in Example 4: annealing temperature 55° C. for 30 sec, extension 72° C. for 90 sec, denaturizing 94° C. for 30 sec and total 30 cycles.

The results of these experiments are presented in Table 1, where P indicates positive, and N, negative. The results suggest that cathepsin K is constitutively expressed in CCL, whereas cathepsin S is not. Only cathepsin K mRNA was found in intact CCL, but both cathespin K and cathepsin S mRNA were found in ruptured CCL. Expression of MMP mRNA (as listed above) is absent in intact ligament and upregulated in aged intact and ruptured CCL, particularly expression of MMP-2 and MMP-9. These findings suggest that the MMP-independent cathepsin K/glycosaminoglycan collagen catabolism pathway [Li et al. 2004] is the main mechanism for collagen turnover in CCL tissue. Use of real-time RT-PCR to quantify gene expression would further help to clarify this, and we have proposed these studies in other grants. It is likely that the MMP-dependent pathway is also activated and that collagen catabolism within ruptured CCL is also mediated by MMPs, particularly MMP-2 and MMP-9 (gelatinases) [Volk et al. 2003]. Up-regulation of cathepsin S in ruptured CCL supports the hypothesis that an immune-mediated mechanism [Nakagawa et al 1999] is activated in dogs with cruciate disease.

TABLE 1

Results of Example 6:

| sample # | | GAPDH | Cat. K | Cat. S | TRAP | MMP-1 | MMP-2 | MMP-3 | MMP-9 | MMP-13 |
|---|---|---|---|---|---|---|---|---|---|---|
| Dogs with CCL rupture | | | | | | | | | | |
| 098665R | CCL | P | P | P | P | P | P | P | P | P |
| 098665R | Pellet | P | P | P | P | P | P | P | P | N |
| 098664L | CCL | P | P | P | P | N | P | N | P | N |
| 098664L | Pellet | P | P | P | P | N | N | N | N | N |
| 098939L | CCL | P | P | P | N | P | P | P | P | P |
| 098939L | Pellet | P | P | P | P | N | P | N | P | N |
| 09277R | CCL | P | P | P | P | P | P | P | P | P |
| 09277R | Pellet | P | P | P | P | P | P | P | P | N |
| 99141 | CCL | P | P | P | P | P | P | P | P | P |
| 99141 | Pellet | P | P | P | P | P | P | N | P | N |
| 099743L | CCl | P | P | P | P | P | P | P | P | P |
| 099743L | Pellet | P | P | P | P | P | P | P | P | N |
| Young normal dogs (beagles) | | | | | | | | | | |
| H04852 | CCL | P | P | N | N | N | N | N | N | N |
| CUTARD | CCL | P | P | N | N | N | N | N | N | N |
| H00815 | CCL | P | P | N | N | N | N | N | N | N |
| CUTATF | CCL | P | P | N | N | N | N | N | N | N |
| CUTAWV | CCL | P | P | N | N | N | N | N | N | N |
| CUTARP | CCL | P | N | N | N | N | N | N | N | N |
| CUT mix | Pellet | P | P | N | N | N | N | N | N | N |
| Older normal dogs (hounds) | | | | | | | | | | |
| Betsy | CCL | P | P | N | N | N | N | P | N | N |
| Betsy | Pellet | P | P | N | N | P | P | N | N | N |
| Donnie | CCL | P | P | N | N | P | N | P | N | N |
| Donnie | Pellet | P | P | N | N | P | P | N | N | N |
| Dolores | CCL | P | P | N | N | N | N | P | N | N |
| Dolores | Pellet | P | P | N | N | P | P | N | N | N |
| Jeoy | CCL | P | P | N | N | N | N | P | N | N |
| Jeoy | Pellet | P | P | N | N | P | P | N | N | N |
| Martha | CCL | P | P | N | N | P | N | P | N | N |
| Martha | Pellet | P | P | N | N | P | P | N | N | N |
| Lexie | CCL | P | P | N | N | N | N | P | N | N |
| Lexie | Pellet | P | P | N | N | P | P | N | N | N |
| Discarded specimens | | | | | | | | | | |
| 094652L | CCL | N | P | N | N | N | N | N | N | N |
| 094652L | Pellet | P | P | P | P | N | P | N | N | N |
| CUPAMJ | CCL | N | P | N | N | N | N | N | N | N |

EXAMPLE 7

Detection of Cathepsin K in Peripheral Blood Mononuclear Cells and Synovial Fluid Cells in Dogs with Cruciate Disease Cathepsin K expression was found in both PBMC (2 of 3 dogs) and synovial fluid cells (3 of 3) dogs with cruciate disease when total RNA was extracted from serum, plasma, PBMC, stifle synovial fluid cells, and the extracellular component of stifle synovial fluid from 3 dogs with CCL rupture. Cathepsin K mRNA was not detected in any extracellular fluid specimens. These data suggest the cathepsin K may be a novel and specific biomarker for the systemic and local inflammatory changes associated with cruciate disease, as we have not detected cathepsin K protein in the intact CCL of 6 young dogs with intact CCL [Muir et al., 2002].

PBMC were isolated from 8 ml samples of peripheral blood using commercially available cell separation tubes (BD VACUTAINER CPT, Becton Dickenson, Franklin Lakes, N.J.) and density gradient centrifugation. Total RNA was prepared from the PBMC using standard RNAzol methodology and commercially available kits. See also U.S. Pat. No. 4,843,155. RT-PCR was carried out as described in the preceding examples.

EXAMPLE 8

Pharmacokinetics Studies of Cathepsin Inhibitors in Canines

Pharmacokinetics of oral NPI 3469 (NAEJA Pharmaceuticals, Edmonton, Alberta, Canada) in the dog. We have conducted a pharmokinetic study in 4 beagles using a single oral dose of NPI 3469 given at 1 mg/kg and pharmacokinetic parameters have been determined. No adverse effects were documented during the treatment period. These results support the dosage of NPI 3469 in the range of 1 to 5 mg/kg orally twice daily in the dog. Monobactam series compounds do not typically have significant adverse effects.

EXAMPLE 9

Cloning and Sequencing of Canine Cathepsin K Gene

Preparation of RNA and Gene Cloning. Total RNA was prepared using standard RNAzol B methodology and commercially available kits. Cells were derived from a stable canine histiocyte cell line is this a commercially available cell line or is there a reference for it?. Preliminary RT-PCR studies have shown that this cell line strongly expresses cathepsin K. cDNA encoding the canine gene was be cloned using polymerase chain reaction (PCR). Briefly, primers were designed for first strand cDNA synthesis and PCR which are based upon areas of high sequence homology for sequences published for other species (human and murine) as follows:

primer (forward primer), 5' CAGCAGGATGTGGGGG 3' (SEQ ID NO: 27)

primer (reverse primer), 5' TCACATCTTGGG-GAAGCTGG 3' (SEQ ID NO:28)

PCR products were sub-cloned into the TA cloning vector (Invitrogen) and sequenced using an automated ABI sequencer; primers for sequencing were from a kit (Invitrogen, cat. No. K4575-J10) and were as follows:

T3 primer 5' ATTAACCCTCACTAAAGGGA 3' (SEQ ID NO:29)

T7 primer 5'GGGATATCACTCAGCATAAT 3' (SEQ ID NO:30).

Clones from at least 3 independent PCR reactions were sequenced to ensure that no errors in the gene were introduced via the PCR process. The results are presented as SEQ. ID. NO: 31. This sequence was compared to the human cathepsin K sequence; homology was determined to be >92%.

It is understood that the invention is not confined to the particular construction and arrangement of parts herein illustrated and described but embraces such modified forms thereof as come within the scope of the following claims.

REFERENCE

Akeson, W. H., Amiel, D., Abel, M. F., Garfin, S. R. and Woo, S. L. (1987). "Effects of immobilization on joints." *Clinical Orthopaedics and Related Research* (219): 28-37.

Akeson, W. H., Woo, S. L., Amiel, D. and Doty, D. H. (1984). "The biology of ligaments." *Rehabilitation of the Injured Knee*. L. Y. Hunter and R. J. Funk. St. Louis, Proc. AAOS: 93-104.

Amiel, D., Akeson, W. H., Harwood, F. L. and Frank, C. B. (1983). "Stress deprivation effect on metabolic turnover of the medial collateral ligament collagen. A comparison between nine- and 12-week immobilization." *Clinical Orthopaedics and Related Research* (172): 265-70.

Amiel, D, Frank, C. and Harwood F. et al. (1984). "Tendons and ligaments: a morphological and biochemical comparison." *J Orthop Res* 1:257-265.

Amiel, D., Ishizue, K. K., Harwood, F. L. et al. (1989). "Injury of the anterior cruciate ligament: the role of collagenase in ligament degeneration." *J Orthop Res* 7:486-493.

Arcasoy, S. M., Latoche, J. D., Gondor, M., Pitt, B. R., and Pilewski, J. M. (1997). Polycations increase the efficiency of adenovirus-mediated gene transfer to epithelial and endothelial cells in vitro. *Gene Ther.* 4, 32-38.

Barenberg, S. A., Filisko, F. E. and Geil, P. H. (1978). "Ultrastructural deformation of collagen." *Connective Tissue Research* 6(1): 25-35.

Bennett, D., Tennant, B., Lewis, D. G., et al. (1988). "A reappraisal of anterior cruciate ligament disease in the dog." *J. Small Anim. Pract* 29:275-297.

Binkley, J. M. and Peat, M. (1986). "The effects of immobilization on the ultrastructure and mechanical properties of the medial collateral ligament of rats." *Clinical Orthopedics and Related Research* (203): 302-308.

Birk, D. E. and Trelstad, R. L. (1986). "Extracellular compartments in tendon morphogenesis: collagen fibril, bundle, and macroaggregate formation." *Journal of Cell Biology* 103(1): 231-40.

Bossard, M. J., Tomaszek, T. A. and Thompson, S. K. et al. (1996). "Proteolytic activity of human osteoclast cathepsin K." *J Biol Chem* 271:12517-12524.

Brodsky, B., Eikenberry, E. F., Belbruno, K. C. and Sterling, K. (1982). "Variations in collagen fibril structure in tendons." *Biopolymers* 21(5): 935-51.

Bromme, D., Kaleta, J (2002). "Thiol-dependent cathepsins: Pathophysiological implications and recent advances in inhibitor design." *Curr Pharm Des* 8:1639-1658.

Bromme, D. and Okamoto, K. (1995). "Human cathepsin O2, a novel cysteine protease highly expressed in osteoclastomas and ovary molecular cloning, sequencing and tissue distribution." *Biological Chemistry Hoppe-Seyler* 376(6): 379-84.

Bromme, D., Okamoto, K., Wang, B. B. and Biroc, S. (1996). "Human cathepsin O2, a matrix protein-degrading cysteine protease expressed in osteoclasts; Functional expression of human cathepsin O2 in Spodoptera frugiperda and characterization of the enzyme." *J Biol Chem* 271(4): 2126-32.

Clark, I. M. and Murphy, G. (1999). Matrix Proteinases. *Dynamics of Bone of Cartilage Metabolism*. M. J. Seibel, S. P. Robins and J. P. Bilezikian. San Diego, Calif., Academic Press: 137-150.

Daniel, D. M., Stone, M. L., Dobson, B. E., Fithian, D. C., Rossman, D. J. and Kaufman, K. R. (1994). "Fate of the ACL-injured patient. A prospective outcome study." *American Journal of Sports Medicine* 22(5): 632-44.

Danylchuk, K. D., Finlay, J. B. and Krcek, J. P. (1978). "Microstructural organization of human and bovine cruciate ligaments." *Clin Orthop* (131): 294-8.

de Rooster, H., Cox, E. and van Bree, H. (2000). "Prevalence and relevance of antibodies to type-I and -II collagen in synovial fluid of dogs with cranial cruciate ligament damage." *Am J Vet Res* 61:1456-1461.

Drake, F. H., Dodds, R. A. and James, I. E. et al. (1996). "Cathepsin K, but not cathepsins B, L, or S, is abundantly expressed in human osteoclasts." *J Biol Chem* 271:12511-12516.

Duval, J. M., Budsberg, S. C., Flo, G. L. and Sammarco, J. L. (1999). "Breed, sex, and body weight as risk factors for rupture of the cranial cruciate ligament in young dogs." *J Am. Vet. Med Assoc* 215:811-814.

Everts, V., Van der Zee, E. and Creemers, L. et al (1996). "Phagocytosis and intracellular digestion of collagen, its role in turnover and remodeling." *Histochem J* 28:229-245.

Foged, N. T., Delaisse, J. M. and Hou, P. et al. (1996). Quantification of collagenolytic activity of isolated osteoclasts by enzyme-linked immunosorbent assay. *J Bone Min Res* 11:226-237.

Freije, J. M., Diez-Itza, I., Balbin, M., Sanchez, L. M., Blasco, R., Tolivia, J. and Lopez-Otin, C. (1994). "Molecular cloning and expression of collagenase-3, a novel human matrix metalloproteinase produced by breast carcinomas." *J Biol Chem* 269(24): 16766-73.

Fruensgaard, S. and Johannsen, H. V. (1989). "Incomplete ruptures of the anterior cruciate ligament." *Journal of Bone and Joint Surgery. British Volume* 71(3): 526-30.

Galloway, R. H. and Lester, S. J. (1995). "Histopathological evaluation of canine stifle joint synovial membrane collected at the time of repair of cranial cruciate ligament rupture." *J Am Anim Hosp Assoc* 31:289-294.

Gamble, J. G., Edwards, C. C. and Max, S. R. (1984). "Enzymatic adaptation in ligaments during immobilization." *American Journal of Sports Medicine* 12(3): 221-8.

Garnero, P., Borel, O., Byrjalsen, I. and Ferreras, M., et al. (1998). "The collagenolytic activity of cathepsin K is unique among mammalian proteinases." *J Biol Chem* 273 (48): 32347-52.

Gelb, B. D., Shi, G. P., Chapman, H. A. and Desnick, R. J. (1996). "Pycnodysostosis, a lysosomal disease caused by cathepsin K deficiency." *Science* 273(5279): 1236-8.

Griffin, D. W. and Vasseur, P. B. (1992). "Synovial fluid analysis in dogs with cranial cruciate ligament rupture." *J Am Anim Hosp Assoc* 28:277-281.

Goldberg, V. M., Burstein, A. and Dawson, M. (1982). "The influence of an experimental immune synovitis on the failure mode and strength of the rabbit anterior cruciate ligament." *J Bone and Joint Surg* 64A:900-906.

Golub, L. M, Lee, H-M and Ryan, M. E. (1998). "Tetracyclines inhibit connective tissue breakdown by multiple non-antimicrobial mechanisms." *Adv Dent Res* 12:12-26.

Gomori, G. (1952). "Microscopic Histochemistry: Principles and Practice," *Chicago, University of Chicago Press,* 137-221.

Greenwald, R. A., Golub, L. M. and Ramamurthy, S., et al. (1998). "In vitro sensitivity of the three mammalian collagenases to tetracycline inhibition: Relationship to bone and cartilage degradation." *Bone* 22:33-38.

Halleen, J. M. et al. (1999). "Intracellular fragmentation of bone resorption products by reactive oxygen species generated by osteoclastic tartrate-resistant acid phosphatase." *J Biol Chem* 274:22907-22910.

Hasty, K. A. et al. (1990). "Human neutrophil collagenase: A distinct gene product with homology to other matrix metalloproteinases." *Journal of Biological Chemistry* 265: 11421-11424.

Hayashi, K. et al. (2003). "Histologic changes in ruptured canine cranial cruciate ligament," *Vet Surg* 32:269-277.

Hayashi K and Frank J. D. et al. (2003). "Evaluation of ligament fibroblast viability in ruptured cranial cruciate ligament of dogs." *Am. J Vet Res* 64:1010-1016.

Hayman, A. R., Bune, A. J. and Bradley, J. R. et al. (2000). "Osteoclastic tartrate-resistant acid phosphatase (Acp 5): Its localization to dendritic cells and diverse murine tissues." *J Histochem Cytochem* 48:219-227.

Hayman, A. R., Jones, S. J. and Boyde, A. et al. (1996). "Mice lacking tartrate-resistant acid phosphatase (Acp 5) have disrupted endochondral ossification and mild osteopetrosis." *Development* 122:3151-3162.

Heffron, L. E. and Campbell, J. R. (1978). "Morphology, histology and functional anatomy of the canine cranial cruciate ligament." *Vet Rec* 102:280-283.

Henriet, P., Rousseau, G. G. and Eeckhout, Y. (1992). "Cloning and sequencing of mouse collagenase cDNA. Divergence of mouse and rat collagenases from the other mammalian collagenases." *FEBS Lett* 310(2): 175-8.

Hewicker-Trautwein, M., Carter, S. D., Bennett, D. and Kelly, D. F. (1999). "Immunocytochemical demonstration of lymphocyte subsets and MHC class II antigen expression in synovial membranes from dogs with rheumatoid arthritis and degenerative joint disease." *Vet Immunol Immunopathol* 67:341-357.

Hillam, R. A. and Skerry, T. M. (1995). "Inhibition of bone resorption and stimulation of formation by mechanical loading of the modeling rat ulna in vivo." *J. Bone Miner Res.,* 10:683-689.

Hou, W. S., Li, Z., Gordon, R. E. and Chan, K. et al. (2001). "Cathepsin K is a critical protease in synovial fibroblast-mediated collagen degradation." *Am J Pathol* 159(6): 2167-77.

Hou W-S, Li W. and Keyszer G. et al. (2002). "Comparison of cathepsins K and S expression within the rhematoid and osteoarthritic synovium." *Arthritis Rheum* 46:663-674.

Inaoka, T., Bilbe, G., Ishibashi, O., Tezuka, K., Kumegawa, M. and Kokubo, T. (1995). "Molecular cloning of human cDNA for cathepsin K: novel cysteine proteinase predominantly expressed in bone." *Biochemical & Biophysical Research Communications* 206(1): 89-96.

Innes, J. F., Bacon, D., Lynch, C. and Pollard, A. (2000). "Long-term outcome of surgery for dogs with cranial cruciate ligament deficiency," *Vet. Rec.* 147:325-328.

Jauernig, S., Schweighauser, A. and Reist, M. et al. (2001). "The effects of doxycycline on nitric oxide and stromolysin production in dogs with cranial cruciate ligament rupture." *Vet Surg* 30:132-139.

Kafienah, W., Bromme, D., Buttle, D. J., Croucher, L. J. and Hollander, A. P. (1998). "Human cathepsin K cleaves native type I and II collagens at the N-terminal end of the triple helix." *Biochem J* 331(Pt 3): 727-32.

Kastelic, J., Galeski, A. and Baer, E. (1978). "The multicomposite structure of tendon." *Connective Tissue Research* 6(1): 11-23.

Kessler, D., Dethlefsen, S., Haase, I. and Plomann, M. et al. (2001). "Fibroblasts in mechanically stressed collagen lattices assume a "synthetic" phenotype." *J Biol Chem* 276 (39): 36575-85.

Knittel, T., Mehde, M., Kobold, D., Saile, B., Dinter, C. and Ramadori, G. (1999). "Expression patterns of matrix metalloproteinases and their inhibitors in parenchymal and non-parenchymal cells of rat liver: regulation by TNF-alpha and TGF-beta1." *Journal of Hepatology* 30(1): 48-60.

Konttinen, Y. T., Mandelin, J., Li, T. F. and Salo, J. et al. (2002). "Acidic cysteine endoproteinase cathepsin K in the degeneration of the superficial articular hyaline cartilage in osteoarthritis." Arthritis Rheum 46(4): 953-60.

Konttinen, Y. T, Takagi, M. and Mandelin, J. et al. (2001). "Acid attack and cathepsin K in bone resorption around total hip replacement prosthesis." *J Bone Min Res* 16:1780-1786.

Lang, P., Schultzberg, M. and Andersson, G. (2001). "Expression and distribution of tartrate-resistant acid phosphatase in the rat nervous system," *J. Histochem Cytochem* 49:379-396.

Lamp, E. C. and Drexler, H. G. (2000). "Biology of tartrate-resistant acid phosphatase." *Leuk Lymphoma* 39:477-484.

Lanza, R. P., Langer, R. and Vacanti, J. (2000). *Principles of Tissue Engineering*. San Diego, Academic Press.

Lawrence, D., Bao, S., and Canfield, P. J. et al. (1998). "Elevation of immunoglobulin deposition in the synovial membrane of dogs with cranial cruciate ligament rupture." *Vet Immunol Immunopathol* 65:89-96.

Lecaille F, Kaletal J, Bromme D. "Human and parasitic papain-like cysteine proteases: Their role in physiology and pathology and recent developments in inhibitor design." Chem Rev 2002; 102:4459-4488.

Li, Z., Hou, W. S. and Bromme, D. (2000). "Collagenolytic activity of cathepsin K is specifically modulated by cartilage-resident chondroitin sulfates." *Biochemistry* 39(3): 529-36.

Li, Z., Hou, W. S., Escalante-Torres, C. R., Gelb, B. D. and Bromme, D. (2002). "Collagenase activity of cathepsin K depends on complex formation with chondroitin sulfate." *J Biol Chem* 277:28669-28676.

Ljusberg. J., Ek-Rylander, B. and Andersson, G. (1999). "Tartrate-resistant purple acid phosphatase is synthesized as a latent proenzyme and activated by cysteine proteinases." *Biochem J* 1999; 343:63-69.

Morris, E. and Lipowitz, A. J. (2001). "Comparison of tibial plateau angles in dogs with and without cranial cruciate ligament injuries." *J. Am. Vet Med. Assoc.*, 218:363-366.

Mudera, V. C., Pleass, R. and Eastwood, M. et al. (2000). "Molecular responses of human dermal fibroblasts to dual cues: contact guidance and mechanical load." *Cell Motil Cytoskeleton* 45(1): 1-9.

Muir, P., Hayashi, K. and Manley, P. A. et al. (2002). "Evaluation of tartrate-resistant acid phosphatase and cathepsin K in ruptured canine cranial cruciate ligament in dogs." *Am. J. Vet Res.*, 63:1279-1284.

Murray, M. M., Martin, S. D. and Martin, T. L. et al. (2000). "Histological changes in the human anterior cruciate ligament after rupture." *J Bone Joint Surg* 82A: 1387-1397.

Nakagawa, T. Y., Brissette, W. H. and Lira, P. D. et al. (1999). "Impaired invariant chain degradation and antigen presentation and diminished collagen-induced arthritis in cathepsin S null mice." *Immunity* 10:207-217.

Narama, I., Masuoka-Nishiyama, M. and Matsuura, T. et al. (1996). "Morphogenesis of degenerative changes predisposing dogs to rupture of the cranial cruciate ligament." *J Vet Med Sci* 58:1091-1097.

Niebauer, G. W., Wolf, B., Bashey, R. I. and Newton, C. D. (1987). "Antibodies to canine collagen types I and II in dogs with spontaneous cruciate ligament rupture and osteoarthritis." *Arthritis Rheum* 1987; 30:319-327

Oddie G W, Schenk, G. and Angel, N. Z. et al. (2000). "Structure, function, and regulation of tartrate-resistant acid phosphatase." *Bone* 27:575-584.

Parak, W. J., Dannohl, S., George, M. and Schuler, M. K. et al. (2000). "Metabolic activation stimulates acid production in synovial fibroblasts." *Journal of Rheumatology* 27(10): 2312-22.

Petersen, W. and Tillmann, B. (1999). "Structure and vascularization of the cruciate ligaments of the human knee." *Anat. Embryol* 200:325-334.

Provenzano, P. P., Hurschler, C. and Vanderby, R. J. (2001). "Microstructural morphology in the transition region between scar and intact residual segments of a healing rat medial collateral ligament." *Connect. Tiss. Res.* 42(2): 123-133.

Quinn, C. O., Scott, D. K. and Brinckerhoff, C. E. et al. (1990). "Rat collagenase. Cloning, amino acid sequence comparison, and parathyroid hormone regulation in osteoblastic cells." *J Biol Chem* 265(36): 22342-7.

Rabkin, E., Aikawa, M. and Stone, J. R., et al. (2001). "Activated interstitial myofibroblasts express catabolic enzymes and mediate matrix remodeling in myxomatous heart valves." *Circulation* 104(21): 2525-32.

Rantakokko, J., Aro, H. T., Savontaus, M. and Vuorio, E. (1996). "Mouse cathepsin K: cDNA cloning and predominant expression of the gene in osteoclasts, and in some hypertrophying chondrocytes during mouse development." *FEBS Letters* 393(2-3): 307-13.

Reno, C., Marchuk, L., Sciore, P., Frank, C. B. and Hart, D. A. (1997). "Rapid isolation of total RNA from small samples of hypocellular, dense connective tissues." *Biotechniques* 22(6): 1082-6.

Saftig, P., Hunziker, E., Wehmeyer, 0. and Jones, S. et al. (1998). "Impaired osteoclastic bone resorption leads to osteopetrosis in cathepsin-K-deficient mice." *Proc Natl Acad Sci USA* 95(23): 13453-8.

Scavelli, T. D., Schrader, S. C. and Matthiesen, D. T. et al. (1990). "Partial rupture of the cranial cruciate ligament of the stifle in dogs: 25 cases (1982-1988)." *J Am Vet Med Assoc* 196:1135-1138.

Schorpp, M., Mattei, M. G., Herr, I., Gack, S., Schaper, J. and Angel, P. (1995). "Structural organization and chromosomal localization of the mouse collagenase type I gene." *Biochem J* 308(Pt 1): 211-7.

Shaffer, C., Roman, S. and Shaffer J. et al. (1999). "Tartrate-resistant acid phosphatase forms complexes with $\alpha_2$-macroglobulin." *J Bone Miner Res* 14:311-318.

Shi, G. P., Chapman, H. A. and Bhairi, S. M. et al. (1995). "Molecular cloning of human cathepsin 0, a novel endoproteinase and homologue of rabbit OC2." *FEBS Letters* 357(2): 129-34.

Spindler, K. P, Clark, S. W. and Nanney, L. B. et al. (1996). "Expression of collagen and matrix metalloproteinases in ruptured human anterior cruciate ligament: an in situ hybridization study." *J Orthop Res.*, 14:857-861.

Stefanini, M., De Martino, C. and Zamboni, L. (1967). "Fixation of ejaculated spermatozoa for electron microscopy." *Nature,* 216:173-174.

Sukhova, G. K., Shi, G. P., Simon, D. I., Chapman, H. A. and Libby, P. (1998). "Expression of the elastolytic cathepsins S and K in human atheroma and regulation of their production in smooth muscle cells." *J Clin Invest* 102(3): 576-83.

Tepel, C., Bromme, D., Herzog, V. and Brix, K. (2000). "Cathepsin K in thyroid epithelial cells: sequence, localization and possible function in extracellular proteolysis of thyroglobulin." *Journal of Cell Science* 113 Pt 24: 4487-98.

Tezuka, K., Tezuka, Y., Maejima, A., Sato, T., Nemoto, K., Kamioka, H., Hakeda, Y. and Kumegawa, M. (1994). "Molecular cloning of a possible cysteine proteinase predominantly expressed in osteoclasts." *J Biol Chem* 269(2): 1106-9.

Thielke, R. J., Cooke, M. E., Graf, B. K., Vailas, A. C. and Vanderby Jr., R. (1994). "Intermittent cyclic loading of canine anterior cruciate ligament explants—a tissue culture study." *Advances in Bioengineering* BED-28: 61-62.

Tsuji, Y., Yamaza, T., Kido, M. A., Goto, T., Nakata, S., Akamine, A., Nakasima, A. and Tanaka, T. (2001). "Expression of cathepsin K mRNA and protein in odontoclasts after experimental tooth movement in the mouse maxilla by in situ hybridization and immunoelectron microscopy." *Cell Tissue Res* 303(3): 359-69.

Vailas, A. C., Zemicke, R. F., Grindeland, R. E. and Li, K. C. (1990). "Suspension effects on rat femur-medial collateral ligament-tibia unit." *American Journal of Physiology* 258(3 Pt 2): R724-8.

Vanderby, R., Jr., Vailas, A. C. and Graf, B. K. et al. (1990). "Acute modification of biomechanical properties of the bone-ligament insertion to rat limb unweighting." *FASEB Journal* 4(8): 2499-505.

Van de Wijngaert, F. P. and Burger, E. H. (1986). "Demonstration of tartrate-resistant acid phosphatase in un-decalcified, glycomethacrylate-embedded mouse bone: a possible marker for (pre) osteoclast identification." *J. Histochem Cytochem.*, 34:1317-1323.

Vasseur, P. B. and Berry, C. R. (1992). "Progression of stifle osteoarthrosis following reconstruction of the cranial cruciate ligament in 21 dogs." *J. Am. Anim. Hosp. Assoc.*, 28:129-136.

Vasseur, P. B, Pool, R. R., Arnozky, S. P. and Lau, R. E. (1985). "Correlative biomechanical and histologic study of the cranial cruciate ligament in dogs." *Am J Vet Res.*,46: 1842-1854.

Verma, I. M. and Somia, N. (1997). Gene therapy—promises, problems and prospects. *Nature* 389, 239-242.

Viidik, A. (1972). "Simultaneous mechanical and light microscopic studies of collagen fibers." *Zeitschriftfur Anatomie und Entwicklungsgeschichte* 136(2): 204-12.

Votta, B. J., Levy, M. A. and Badger, A. et al. (1997). "Peptide aldehyde inhibitors of cathepsin K inhibit bone resorption in vitro and in vivo." *J Bone Miner Res* 12: 1396-1406.

Welgus, H. G., Jeffrey, J. J., Stricklin, G. P. and Eisen, A. Z. (1982). "The gelatinolytic activity of human skin fibroblast collagenase." *Journal of Biological Chemistry* 257(19): 11534-11539.

Whitehair, J. G., Vasseur, P. B. and Willits, N. H. (1993). "Epidemiology of cranial cruciate ligament rupture in dogs." *J. Am. Vet. Med Assoc*2O3:1016-1019.

Woo, S. L., Gomez, M. A. and Sites, T. J. et al. (1987). "The biomechanical and morphological changes in the medial collateral ligament of the rabbit after immobilization and remobilization." *J Bone Joint Surg Am* 69(8): 1200-11.

Yu, L. P. Jr, Smith, G. N. and Brandt, K. D., et al. (1992). "Reduction in the severity of canine osteoarthritis by prophylactic treatment with oral doxycycline." *Arthritis Rheum* 35:1150-1159.

Xia, L. et al. (1999). "Localization of rat cathepsin K in osteoclasts and resorption pits: inhibition of bone resorption and cathepsin K-activity by peptidyl vinyl sulfones." *Biological Chemistry* 380(6): 679-87

What is claimed is:

1. A method of treating degenerative ligament disease in a subject in need thereof, the method comprising decreasing activity of cathepsin S in an affected ligament in the subject, by administering to the subject an amount of a cathepsin S inhibitor wherein the amount is sufficient to decrease the activity of cathepsin S.

2. A method of treating degenerative ligament disease in a subject in need thereof, the method comprising decreasing activity of cathepsin S in an affected ligament in the subject, by administering to the subject an amount of a cathepsin S inhibitor wherein the amount is sufficient to decrease the activity of cathepsin S, wherein the inhibitor is selected from the group consisting of NPI-3469 and pharmaceutically acceptable salts thereof.

3. A method of treating degenerative ligament disease in a subject in need thereof, the method comprising decreasing activity of an enzyme selected from the group consisting of cathepsin K and cathepsin S in an affected ligament in the subject, by administering to the subject an amount of an inhibitor selected from the group consisting of cathepsin K inhibitors, cathepsin S inhibitors, and combinations thereof, wherein the amount is sufficient to decrease the activity of cathepsin K or cathepsin S, wherein the inhibitor is selected from the group consisting of 4-dedimethylaminosancycline, NPI-3469, SB-357114, pharmaceutically acceptable salts thereof, and combinations thereof.

* * * * *

SEQUENCE LISTING

```
<160> NUMBER OF SEQ ID NOS: 32

<210> SEQ ID NO 1
<211> LENGTH: 22
<212> TYPE: DNA
<213> ORGANISM: ARTIFICIAL SEQUENCE
<220> FEATURE:
<223> OTHER INFORMATION: FORWARD PRIMER FOR RAT CATHEPSIN K

<400> SEQUENCE: 1
aaagaacatg gtgacttcta cc                                              22

<210> SEQ ID NO 2
<211> LENGTH: 19
<212> TYPE: DNA
<213> ORGANISM: ARTIFICIAL SEQUENCE
<220> FEATURE:
<223> OTHER INFORMATION: REVERSE PRIMER FOR RAT CATHEPSIN K

<400> SEQUENCE: 2
actggattcc ttgaacgtc                                                  19

<210> SEQ ID NO 3
<211> LENGTH: 22
<212> TYPE: DNA
<213> ORGANISM: ARTIFICIAL SEQUENCE
<220> FEATURE:
```

-continued

<223> OTHER INFORMATION: PCR FORWARD PRIMER FOR CATHEPSIN K

<400> SEQUENCE: 3
tgcgaccgtg ataatgtgaa cc                                              22

<210> SEQ ID NO 4
<211> LENGTH: 21
<212> TYPE: DNA
<213> ORGANISM: ARTIFICIAL SEQUENCE
<220> FEATURE:
<223> OTHER INFORMATION: PCR REVERSE PRIMER FOR CATHEPSIN K

<400> SEQUENCE: 4
atgggctggc tggcttgaat c                                               21

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: PCR PRIMER FORWARD FOR GAPDH

<400> SEQUENCE: 5
gactgtggat ggcccctctg                                                 20

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: PCR REVERSE PRIMER FOR GAPDH

<400> SEQUENCE: 6
cgcctgcttc accaccttct                                                 20

<210> SEQ ID NO 7
<211> LENGTH: 22
<212> TYPE: DNA
<213> ORGANISM: ARTIFICIAL SEQUENCE
<220> FEATURE:
<223> OTHER INFORMATION: PCR FORWARD PRIMER FOR MMP-2

<400> SEQUENCE: 7
ggtcgcagtg atggcttcct ct                                              22

<210> SEQ ID NO 8
<211> LENGTH: 22
<212> TYPE: DNA
<213> ORGANISM: ARTIFICIAL SEQUENCE
<220> FEATURE:
<223> OTHER INFORMATION: PCR REVERSE PRIMER FOR MMP-2

<400> SEQUENCE: 8
cacaccacac cttgccatcg tt                                              22

<210> SEQ ID NO 9
<211> LENGTH: 23
<212> TYPE: DNA
<213> ORGANISM: ARTIFICIAL SEQUENCE
<220> FEATURE:
<223> OTHER INFORMATION: PCR FORWARD PRIMER FOR CATHEPSIN K

<400> SEQUENCE: 9
cagtgtggtt cctgttgggc ttt                                             23

<210> SEQ ID NO 10

```
<211> LENGTH: 20
<212> TYPE: DNA
<213> ORGANISM: ARTIFICIAL SEQUENCE
<220> FEATURE:
<223> OTHER INFORMATION: PCR REVERSE PRIMER FOR CATHEPSIN K

<400> SEQUENCE: 10
tcacatcttg gggaagctgg                                                     20

<210> SEQ ID NO 11
<211> LENGTH: 17
<212> TYPE: DNA
<213> ORGANISM: ARTIFICIAL SEQUENCE
<220> FEATURE:
<223> OTHER INFORMATION: TRAP FORWARD PRIMER

<400> SEQUENCE: 11
cagctgtcct ggctcaa                                                        17

<210> SEQ ID NO 12
<211> LENGTH: 17
<212> TYPE: DNA
<213> ORGANISM: ARTIFICIAL SEQUENCE
<220> FEATURE:
<223> OTHER INFORMATION: TRAP REVERSE PRIMER

<400> SEQUENCE: 12
tagccgttgg ggacctt                                                        17

<210> SEQ ID NO 13
<211> LENGTH: 20
<212> TYPE: DNA
<213> ORGANISM: ARTIFICIAL SEQUENCE
<220> FEATURE:
<223> OTHER INFORMATION: CATHEPSIN S FORWARD PRIMER

<400> SEQUENCE: 13
cgtctcatct gggaaaagaa                                                     20

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: CATHEPSIN S REVERSE PRIMER

<400> SEQUENCE: 14
gctttgtagg gataggaagc                                                     20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: MMP-1 FORWARD PRIMER

<400> SEQUENCE: 15
ttcggggaga agtgatgttc                                                     20

<210> SEQ ID NO 16
<211> LENGTH: 21
<212> TYPE: DNA
<213> ORGANISM: ARTIFICIAL SEQUENCE
<220> FEATURE:
<223> OTHER INFORMATION: MMP-1 REVERSE PRIMER

<400> SEQUENCE: 16
```

-continued gcagttgaac cagctattag c                                              21

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: MMP-2 FORWARD PRIMER

<400> SEQUENCE: 17
atggcaaata cggcttctgc                                                20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: MMP-2 REVERSE PRIMER

<400> SEQUENCE: 18
tgcagctctc atgcttgttg                                                20

<210> SEQ ID NO 19
<211> LENGTH: 20
<212> TYPE: DNA
<213> ORGANISM: ARTIFICIAL SEQUENCE
<220> FEATURE:
<223> OTHER INFORMATION: MMP-3 FORWARD PRIMER

<400> SEQUENCE: 19
acagtggtcc tgtcgttgaa                                                20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: MMP-3 REVERSE PRIMER

<400> SEQUENCE: 20
agtcacctcc ttccagacat                                                20

<210> SEQ ID NO 21
<211> LENGTH: 20
<212> TYPE: DNA
<213> ORGANISM: ARTIFICIAL SEQUENCE
<220> FEATURE:
<223> OTHER INFORMATION: MMP-9 FORWARD PRIMER

<400> SEQUENCE: 21
cgctatggct acactcaagt                                                20

<210> SEQ ID NO 22
<211> LENGTH: 20
<212> TYPE: DNA
<213> ORGANISM: ARTIFICIAL SEQUENCE
<220> FEATURE:
<223> OTHER INFORMATION: MMP-9 REVERSE PRIMER

<400> SEQUENCE: 22
aagtgatgtc gttgtggtgc                                                20

<210> SEQ ID NO 23
<211> LENGTH: 20
<212> TYPE: DNA
<213> ORGANISM: ARTIFICIAL SEQUENCE
<220> FEATURE:

<223> OTHER INFORMATION: MMP-13 FORWARD PRIMER

<400> SEQUENCE: 23
ctgaggaaga cttccagctt                                                   20

<210> SEQ ID NO 24
<211> LENGTH: 20
<212> TYPE: DNA
<213> ORGANISM: ARTIFICIAL SEQUENCE
<220> FEATURE:
<223> OTHER INFORMATION: MMP-13 REVERSE PRIMER

<400> SEQUENCE: 24
ttggaccact tgagagttcg                                                   20

<210> SEQ ID NO 25
<211> LENGTH: 20
<212> TYPE: DNA
<213> ORGANISM: ARTIFICIAL SEQUENCE
<220> FEATURE:
<223> OTHER INFORMATION: GAPDH FORWARD PRIMER

<400> SEQUENCE: 25
accacagtcc atgccatcac                                                   20

<210> SEQ ID NO 26
<211> LENGTH: 20
<212> TYPE: DNA
<213> ORGANISM: ARTIFICIAL SEQUENCE
<220> FEATURE:
<223> OTHER INFORMATION: GAPDH REVERSE PRIMER

<400> SEQUENCE: 26
tccaccaccc tgttgctgta                                                   20

<210> SEQ ID NO 27
<211> LENGTH: 16
<212> TYPE: DNA
<213> ORGANISM: ARTIFICIAL SEQUENCE
<220> FEATURE:
<223> OTHER INFORMATION: FORWARD PRIMER FOR CANINE CATHEPSIN K

<400> SEQUENCE: 27
cagcaggatg tggggg                                                       16

<210> SEQ ID NO 28
<211> LENGTH: 20
<212> TYPE: DNA
<213> ORGANISM: ARTIFICIAL SEQUENCE
<220> FEATURE:
<223> OTHER INFORMATION: REVERSE PRIMER FOR CANINE CATHEPSIN K

<400> SEQUENCE: 28
tcacatcttg gggaagctgg                                                   20

<210> SEQ ID NO 29
<211> LENGTH: 19
<212> TYPE: DNA
<213> ORGANISM: ARTIFICIAL SEQUENCE
<220> FEATURE:
<223> OTHER INFORMATION: T3 PRIMER 5'

<400> SEQUENCE: 29
attaaccctc actaaagga                                                    19

<210> SEQ ID NO 30

```
<211> LENGTH: 20
<212> TYPE: DNA
<213> ORGANISM: ARTIFICIAL SEQUENCE
<220> FEATURE:
<223> OTHER INFORMATION: T7 PRIMER 5'

<400> SEQUENCE: 30
gggatatcac tcagcataat                                                 20

<210> SEQ ID NO 31
<211> LENGTH: 1001
<212> TYPE: DNA
<213> ORGANISM: Canis familiaris
<220> FEATURE:
<221> NAME/KEY: CDS
<222> LOCATION: (9)..(1001)

<400> SEQUENCE: 31
```

| | | | | | | | | | | | | | | | |
|---|---|---|---|---|---|---|---|---|---|---|---|---|---|---|---|
| tcagcagg | atg | tgg | ggg | ctt | gag | gtt | cta | ctg | ctg | ctg | ccc | atg | gca | agc | 50 |
| | Met | Trp | Gly | Leu | Glu | Val | Leu | Leu | Leu | Leu | Pro | Met | Ala | Ser | |
| | 1 | | | 5 | | | | | 10 | | | | | | |
| ttt | gct | cta | tat | cct | gag | gag | ata | ctg | gac | acc | caa | tgg | gac | ctt | tgg | 98 |
| Phe | Ala | Leu | Tyr | Pro | Glu | Glu | Ile | Leu | Asp | Thr | Gln | Trp | Asp | Leu | Trp |
| 15 | | | | 20 | | | | | 25 | | | | | 30 | |
| aag | aag | acc | tac | agg | aag | cag | tat | aat | agc | aag | gtg | gat | gaa | ctc | tct | 146 |
| Lys | Lys | Thr | Tyr | Arg | Lys | Gln | Tyr | Asn | Ser | Lys | Val | Asp | Glu | Leu | Ser |
| | | | | 35 | | | | | 40 | | | | | 45 | |
| cgg | cgt | tta | att | tgg | gaa | aaa | aac | ttg | aag | cat | att | tct | atc | cat | aat | 194 |
| Arg | Arg | Leu | Ile | Trp | Glu | Lys | Asn | Leu | Lys | His | Ile | Ser | Ile | His | Asn |
| | 50 | | | | | 55 | | | | | 60 | | | | |
| ctt | gaa | gcc | tct | ctt | ggt | gtc | cat | aca | tat | gaa | ctg | gcc | atg | aac | cac | 242 |
| Leu | Glu | Ala | Ser | Leu | Gly | Val | His | Thr | Tyr | Glu | Leu | Ala | Met | Asn | His |
| 65 | | | | | 70 | | | | | 75 | | | | | |
| ttg | ggt | gac | atg | acc | agt | gaa | gag | gtg | gtt | cag | aag | atg | act | gga | ctc | 290 |
| Leu | Gly | Asp | Met | Thr | Ser | Glu | Glu | Val | Val | Gln | Lys | Met | Thr | Gly | Leu |
| | 80 | | | | 85 | | | | | 90 | | | | | |
| aaa | gta | ccc | ccc | tct | cac | tcc | cgc | agt | aat | gat | act | ctc | tat | atc | cca | 338 |
| Lys | Val | Pro | Pro | Ser | His | Ser | Arg | Ser | Asn | Asp | Thr | Leu | Tyr | Ile | Pro |
| 95 | | | | 100 | | | | | 105 | | | | | 110 | |
| gac | tgg | gaa | agc | aga | gcc | cca | gac | tcc | gtt | gat | tat | cga | aag | aaa | gga | 386 |
| Asp | Trp | Glu | Ser | Arg | Ala | Pro | Asp | Ser | Val | Asp | Tyr | Arg | Lys | Lys | Gly |
| | | | 115 | | | | | 120 | | | | | 125 | | |
| tat | gtt | act | cct | gtc | aag | aac | cag | ggt | cag | tgt | ggt | tcc | tgt | tgg | gct | 434 |
| Tyr | Val | Thr | Pro | Val | Lys | Asn | Gln | Gly | Gln | Cys | Gly | Ser | Cys | Trp | Ala |
| | | 130 | | | | | 135 | | | | | 140 | | | |
| ttt | agc | tct | gtg | ggt | gcc | ctg | gag | ggc | caa | ctc | aag | aag | aaa | act | ggc | 482 |
| Phe | Ser | Ser | Val | Gly | Ala | Leu | Glu | Gly | Gln | Leu | Lys | Lys | Lys | Thr | Gly |
| | 145 | | | | | 150 | | | | | 155 | | | | |
| aaa | ctc | tta | aat | ctg | agt | ccc | cag | aac | ctg | gtg | gac | tgt | gtc | tct | gag | 530 |
| Lys | Leu | Leu | Asn | Leu | Ser | Pro | Gln | Asn | Leu | Val | Asp | Cys | Val | Ser | Glu |
| 160 | | | | | 165 | | | | | 170 | | | | | |
| aat | gat | ggc | tgt | gga | gga | ggc | tac | atg | acc | aat | gcc | ttc | cag | tat | gtg | 578 |
| Asn | Asp | Gly | Cys | Gly | Gly | Gly | Tyr | Met | Thr | Asn | Ala | Phe | Gln | Tyr | Val |
| 175 | | | | 180 | | | | | 185 | | | | | 190 | |
| cag | aag | aac | cgg | ggc | att | gac | tct | gaa | gat | gcc | tac | cca | tat | gtg | gga | 626 |
| Gln | Lys | Asn | Arg | Gly | Ile | Asp | Ser | Glu | Asp | Ala | Tyr | Pro | Tyr | Val | Gly |
| | | | 195 | | | | | 200 | | | | | 205 | | |
| cag | gat | gaa | agc | tgt | atg | tac | aac | cca | aca | ggc | aag | gca | gct | aag | tgc | 674 |
| Gln | Asp | Glu | Ser | Cys | Met | Tyr | Asn | Pro | Thr | Gly | Lys | Ala | Ala | Lys | Cys |
| | | 210 | | | | | 215 | | | | | 220 | | | |
| aga | ggg | tac | aga | gag | atc | cct | gag | ggg | aat | gag | aaa | gcc | ctg | aag | agg | 722 |
| Arg | Gly | Tyr | Arg | Glu | Ile | Pro | Glu | Gly | Asn | Glu | Lys | Ala | Leu | Lys | Arg |
| | 225 | | | | | 230 | | | | | 235 | | | | |

```
gca gtg gcc cga gtg gga ccc atc tct gtg gcc att gat gca agc ctg    770
Ala Val Ala Arg Val Gly Pro Ile Ser Val Ala Ile Asp Ala Ser Leu
    240                 245                 250 acc tct ttc cag ttt tac agc aaa ggt gtg tac tac gat gaa aac tgt    818
Thr Ser Phe Gln Phe Tyr Ser Lys Gly Val Tyr Tyr Asp Glu Asn Cys
255                 260                 265                 270 aat agc gat aat ctg aac cat gca gtt ttg gca gtg gga tat ggc atc    866
Asn Ser Asp Asn Leu Asn His Ala Val Leu Ala Val Gly Tyr Gly Ile
                275                 280                 285 cag aaa gga aac aag cac tgg ata att aaa aac agc tgg gga gaa aac    914
Gln Lys Gly Asn Lys His Trp Ile Ile Lys Asn Ser Trp Gly Glu Asn
            290                 295                 300 tgg gga aac aaa ggc tat atc ctc atg gct cgg aat aag aac aac gct    962
Trp Gly Asn Lys Gly Tyr Ile Leu Met Ala Arg Asn Lys Asn Asn Ala
        305                 310                 315 tgc ggc att gcc aac ctg gcc agc ttc ccc aag atg tga                1001
Cys Gly Ile Ala Asn Leu Ala Ser Phe Pro Lys Met
    320                 325                 330

<210> SEQ ID NO 32
<211> LENGTH: 330
<212> TYPE: PRT
<213> ORGANISM: Canis familiaris

<400> SEQUENCE: 32

Met Trp Gly Leu Glu Val Leu Leu Leu Pro Met Ala Ser Phe Ala
1               5                   10                  15

Leu Tyr Pro Glu Glu Ile Leu Asp Thr Gln Trp Asp Leu Trp Lys Lys
                20                  25                  30

Thr Tyr Arg Lys Gln Tyr Asn Ser Lys Val Asp Glu Leu Ser Arg Arg
            35                  40                  45

Leu Ile Trp Glu Lys Asn Leu Lys His Ile Ser Ile His Asn Leu Glu
        50                  55                  60

Ala Ser Leu Gly Val His Thr Tyr Glu Leu Ala Met Asn His Leu Gly
65                  70                  75                  80

Asp Met Thr Ser Glu Glu Val Val Gln Lys Met Thr Gly Leu Lys Val
                85                  90                  95

Pro Pro Ser His Ser Arg Ser Asn Asp Thr Leu Tyr Ile Pro Asp Trp
            100                 105                 110

Glu Ser Arg Ala Pro Asp Ser Val Asp Tyr Arg Lys Lys Gly Tyr Val
        115                 120                 125

Thr Pro Val Lys Asn Gln Gly Gln Cys Gly Ser Cys Trp Ala Phe Ser
130                 135                 140

Ser Val Gly Ala Leu Glu Gly Gln Leu Lys Lys Thr Gly Lys Leu
145                 150                 155                 160

Leu Asn Leu Ser Pro Gln Asn Leu Val Asp Cys Val Ser Glu Asn Asp
                165                 170                 175

Gly Cys Gly Gly Gly Tyr Met Thr Asn Ala Phe Gln Tyr Val Gln Lys
            180                 185                 190

Asn Arg Gly Ile Asp Ser Glu Asp Ala Tyr Pro Tyr Val Gly Gln Asp
        195                 200                 205

Glu Ser Cys Met Tyr Asn Pro Thr Gly Lys Ala Ala Lys Cys Arg Gly
    210                 215                 220

Tyr Arg Glu Ile Pro Glu Gly Asn Glu Lys Ala Leu Lys Arg Ala Val
225                 230                 235                 240

Ala Arg Val Gly Pro Ile Ser Val Ala Ile Asp Ala Ser Leu Thr Ser
                245                 250                 255
```

```
Phe Gln Phe Tyr Ser Lys Gly Val Tyr Tyr Asp Glu Asn Cys Asn Ser
            260                 265                 270

Asp Asn Leu Asn His Ala Val Leu Ala Val Gly Tyr Gly Ile Gln Lys
        275                 280                 285

Gly Asn Lys His Trp Ile Ile Lys Asn Ser Trp Gly Glu Asn Trp Gly
    290                 295                 300

Asn Lys Gly Tyr Ile Leu Met Ala Arg Asn Lys Asn Asn Ala Cys Gly
305                 310                 315                 320

Ile Ala Asn Leu Ala Ser Phe Pro Lys Met
                325             330
```